(12) United States Patent
Park

(10) Patent No.: US 10,137,070 B2
(45) Date of Patent: Nov. 27, 2018

(54) COMPOSITION INCLUDING IONONE OR SALT THEREOF AS ACTIVE INGREDIENT AND HAVING EFFECT OF ENHANCING SKIN MOISTURIZING, EXFOLIATING SKIN, IMPROVING SKIN ELASTICITY, INHIBITING ERYTHEMA, IMPROVING SKIN WRINKLES, OR ALLEVIATING SKIN PHOTOAGING

(71) Applicant: Industry-Academic Cooperation Foundation, Yonsei University, Seoul (KR)

(72) Inventor: Tae Sun Park, Seoul (KR)

(73) Assignee: YONSEI UNIVERSITY TECHNOLOGY HOLDINGS, INC., Incheon (KR)

( * ) Notice: Subject to any disclaimer, the term of this patent is extended or adjusted under 35 U.S.C. 154(b) by 0 days.

(21) Appl. No.: 15/629,517

(22) Filed: Jun. 21, 2017

(65) Prior Publication Data
US 2017/0367954 A1    Dec. 28, 2017

(30) Foreign Application Priority Data

Jun. 22, 2016  (KR) .................. 10-2016-0077927

(51) Int. Cl.
| A61K 8/35 | (2006.01) |
| A61K 8/67 | (2006.01) |
| A23L 33/10 | (2016.01) |
| A61Q 19/00 | (2006.01) |
| A61Q 19/08 | (2006.01) |

(52) U.S. Cl.
CPC ............... *A61K 8/35* (2013.01); *A23L 33/10* (2016.08); *A61K 8/676* (2013.01); *A61Q 19/007* (2013.01); *A61Q 19/08* (2013.01); *A23V 2002/00* (2013.01); *A61K 2800/28* (2013.01)

(58) Field of Classification Search
CPC ........... A61K 8/35; A61K 8/678; A23L 33/10; A61Q 19/007
See application file for complete search history.

(56) References Cited

U.S. PATENT DOCUMENTS 5,759,556 A * 6/1998 Burger ............... A61K 8/34
424/401

FOREIGN PATENT DOCUMENTS

WO    WO 2001008650    * 2/2001

OTHER PUBLICATIONS

Bateman et al., "Collagen Superfamily," *Extracellular Matrix*, 2 (1996): 22-26.
Cadby et al., "Consumer Exposure to Fragrance Ingredients: Providing Estimates for Safety Evaluation," *Regulatory Toxicology and Pharmacology*, 36 (2002) 246-252.
Chung et al., "γ-Linolenic Acid in Borage Oil Reverses Epidermal Hyperproliferation in Guinea Pigs," *The Journal of Nutrition*, 132.10 (2000): 3090-3097.
Dy et al., "Augmentation of Ultraviolet B Radiation-induced Tumor Necrosis Factor Production by the Epidermal Platelet-activating Factor Receptor," *The Journal of Biological Chemistry*, 274.38 (1999): 26917-26921.
Findik et al., "Synthesis of Terpenoid-Like Bischalcones from α- and β-Ionones and Their Biological Activites," *Synthetic Communications*, 39.24 (2009): 4362-4374.
Kang et al., "Inflammation and Extracellular Matrix Degradation Mediated by Activated Transcription Factors Nuclear Factor-κB and Activator Protein-1 in Inflammatory Acne Lesions in Vivo," *The American Journal of Pathology* 166.6 (2005): 1691-1699.
Moskowitz, Roland, "Role of Collagen Hydrolysate in Bone and Joint Disease," *Seminars in Arthritis and Rheumatism*, 30.2 (2000): 87-99.
Pei et al., "Expression of Collagen Type I, II, and III in loose body of osteoarthritis," *Journal of Orthopaedic Science*, 5 (2000): 288-293.
Sachsenmaler et al., "Involvement of Growth Factor Receptors in the Mammalian UVC Response," *Cell*, 78 (1994): 963-972.
Sporn et al., "The effect of certain chemical compounds used in the food industry on the enzymatic activity of the liver," *Studii Cercetari Biochim,*, 7 (1964):23-34.
Sporn et al., "The toxicity of butyl acetate, methyl naphthyl ketone and ionone," *Igiena*, 12 (1963), 437-445.
Tanno et al., "Nicotinamide increases biosynthesis of ceramides as well as other stratum corneum lipids to improve the epidermal barrier," *British Journal of Dermatology*, 143 (2000): 524-531.

* cited by examiner

*Primary Examiner* — Shirley V Gembeh
(74) *Attorney, Agent, or Firm* — Norton Rose Fulbright US LLP

(57) ABSTRACT

Provided herein are a cosmetic composition, a health functional food composition, a pharmaceutical composition, and a quasi-drug composition that include ionone or a salt thereof as an active ingredient and have an effect of enhancing skin moisturizing, exfoliating skin, improving skin elasticity, inhibiting erythema, improving skin wrinkles, or alleviating skin photoaging. The ionone or the salt thereof has an activity of enhancing skin moisture content, reducing skin moisture evaporation, increasing procollagen secretion, promoting collagen biosynthesis, suppressing collagen fiber damage, suppressing collagen fiber decomposition, inhibiting erythema, and suppressing the thickening of a skin epidermis layer, and thus may be usefully used as a material of functional cosmetics, health functional foods, pharmaceuticals, quasi-drugs, or the like that provide an effect of enhancing skin moisturizing, exfoliating skin, improving skin elasticity, inhibiting erythema, improving skin wrinkles, and/or alleviating skin photoaging.

5 Claims, 8 Drawing Sheets
Specification includes a Sequence Listing.

COMPOSITION INCLUDING IONONE OR SALT THEREOF AS ACTIVE INGREDIENT AND HAVING EFFECT OF ENHANCING SKIN MOISTURIZING, EXFOLIATING SKIN, IMPROVING SKIN ELASTICITY, INHIBITING ERYTHEMA, IMPROVING SKIN WRINKLES, OR ALLEVIATING SKIN PHOTOAGING

CROSS-REFERENCE TO RELATED APPLICATION

This application claims priority to and the benefit of Korean Patent Application No. 10-2016-0077927, filed on Jun. 22, 2016, the disclosure of which is incorporated herein by reference in its entirety.

BACKGROUND

1. Field of the Invention

The present disclosure relates to a composition including ionone or a salt thereof as an active ingredient, and more particularly, to a cosmetic composition, a health functional food composition, a pharmaceutical composition, and a quasi-drug composition that use ionone or a salt thereof having an activity of enhancing skin moisture content, reducing skin moisture evaporation, increasing procollagen secretion, promoting collagen biosynthesis, suppressing collagen fiber damage, suppressing collagen fiber decomposition, inhibiting erythema, and suppressing the thickening of a skin epidermis layer, and thus having an effect of enhancing skin moisturizing, exfoliating skin, improving skin elasticity, inhibiting erythema, improving skin wrinkles, and/or alleviating skin photoaging.

2. Discussion of Related Art

With the recent advances in medical technology, life expectancy has extended, the quality of life has improved, and desire for a beautiful life has increased, and, accordingly, interest in skin care and health has increased. Thus, various beauty functional cosmetics have been developed for the purpose of maintaining healthy skin, and, especially, research into the prevention, alleviation and reduction of skin wrinkles is actively ongoing. In addition, there is a limitation on cosmetic ingredients supplying nutrients by reaching the skin dermis and a change in perception has recently occurred such that skin beauty enhancement effects may be obtained by supplying nutrients or functional ingredients to skin through food intake, and, accordingly, research into discovering inner beauty food substances is also actively ongoing (Chung, S. et al., γ-Linolenic acid in borage oil reverses epidermal hyperproliferation in guinea pigs. J Nutr, 132, 3090-3097, 2002; Tanno, O. et al., Nicotinamide increases biosynthesis of ceramides as well as other stratum corneum lipids to improve the epidermal permeability barrier. Br J Derm, 143, 524-531, 2000).

The skin is largely composed of three layers: the epidermis, dermis, and hypodermis. The epidermis, especially the stratum corneum, which is the outermost layer of the epidermis, acts as a skin barrier to inhibit the loss of moisture and electrolytes from the skin, while the dermis layer maintains skin elasticity and supports a structure thereof through synthesis of collagen and elastin. That is, collagen and elastin are the main proteins produced in fibroblasts, which are involved in the mechanical durability of the skin, and the binding force and elasticity of the tissue (Moskowitz, R. W. et al, Role of collagen hydrolysate in bone and joint disease, Semin Arthritis Rheu, 30: 87, 2000). Collagen constitutes various isoforms according to their morphological and structural characteristics, and a total of 28 collagen isotypes is present in human tissues. Among these collagen isotypes, collagen types 1, 3, 4, 6, 7, 13, 14, 17, and the like are known as collagen present in skin tissue. Collagen types 1 and 3 form matrix components of the dermis layer, and collagen type 7 is the major component of the dermis and epidermis junction (Pei, M. et al., Expression of collagen type I, II and III in loose body of osteoarthritis, J. Orthop. Sci., 5: 288, 2000).

In skin connective tissue, type I collagen is the most abundant of extracellular matrix proteins and other proteins, such as elastin, fibronectin, integrins, fibrillin, proteoglycans, and the like, are present. Newly synthesized procollagen is secreted into the extracellular space of skin cells through an enzymatic reaction and then forms a microfibril of a triple helix configuration, and microfibrils bind to leucine-rich small proteoglycans to form a fibril. Consequently, the fibrils formed as described above gather to form collagen fibers that provide the binding force and elasticity of the skin (Bateman, J. F. et al., Collagen superfamily. Extracellular matrix, Harwood, N.Y., 2, 22-26, 1996).

Skin aging is known to be caused by a decrease in the content of collagen, which is a protein mostly present in skin dermis tissue. Collagen imparts tension and strength to the skin, and thus collagen reduction has much to do with skin aging and wrinkle formation. Skin aging is largely divided into endogenous aging by physiological aging and photoaging caused by continuous ultraviolet radiation (UV) exposure. Repeated exposure to ultraviolet light results in increased collagenase and denaturation and destruction of collagen fibers, thereby reducing skin elasticity and promoting the production of wrinkles. In other words, the generation of reactive oxygen species (ROS) is increased in skin tissue continuously exposed to ultraviolet light, and the latter promotes the production of proinflammatory cytokines through signaling pathways mediated by growth factor receptors (EGF-R), tumor necrosis factor (TNF)-receptors, and the like (Sachsenmaier, C. et al., Involvement of growth factor receptors in the mammalian UVC response. Cell, 78:963-972, 1994; Dy, L. C. et al., Augmentation of ultraviolet B radiation-induced tumor necrosis factor production by the epidermal platelet-activating factor receptor. J. Biol. Chem.: 274, 26917-2692, 1999). Activation of these receptors results in continuous phosphorylation, which activates proteins that mediate downstream signaling, including mitogen-activated protein kinase (MAPK), resulting in the induction of inflammatory responses by activating transcription factors such as activator protein-1 (AP-1) and nuclear factor κB (NF-κB) and the promotion of an activity of collagenase such as matrix metalloproteinase (MMPs), thereby reducing skin elasticity and promoting wrinkle formation (Kang, S. et al., Inflammation and extracellular matrix degradation mediated by activated transcription factors nuclear factor-kB and activator protein-1 in inflammatory acne lesions in vivo. Am J. Pathol., 166: 1691-1699, 2005). AP-1 regulates the expression of a number of genes involved in cell growth and differentiation and strongly regulates the expression of some MMPs. Among the MMPs, expression of which is regulated by AP-1, MMP-1 is known as collagenase 1, and types 1 and 3 collagen are used as substrates.

Meanwhile, ionone is a fragrance ingredient mainly contained in *Rubus idaeus* (Raspberry), *Daucus carota* subsp.

*Sativus* (Carrot), *Prunus dulcis* (Almond), and *Menta* (Herb) and mainly produces the scent of flowers. Ionone is mainly used as an ingredient of shampoo, soap, cleaning products, body lotion, cosmetics, shower gel, and hair spray, is listed as a flavoring agent in the Korea Food and Drug Administration (KFDA) and US FDA food additive database, and is mainly used in soft drinks, ice cream, chewing gums, and the like. In research on the physiological activity of ionone, it has been reported that ionone has a strong antimicrobial activity against microorganisms harmful to the human body (Findic et al, Synthesis of Terpenoid-Like Bischalcones from α- and β-Ionones and Their Biological Activities, Synthetic Communications, 39: 4362-4374, 2009), but no other physiological activity has been reported.

The inventors of the present disclosure had conducted studies on developing a food or cosmetic material effective in reducing wrinkles by inhibiting the action of collagenase in natural products with low side effects and promoting the synthesis of collagen and, as a result, verified that ionone had an effect of enhancing skin moisturizing, exfoliating skin, enhancing skin elasticity, inhibiting erythema, improving skin wrinkles, and/or alleviating skin photoaging, thus completing the invention.

SUMMARY OF THE INVENTION

One or more embodiments provide a cosmetic composition having an effect of enhancing skin moisturizing, exfoliating skin, enhancing skin elasticity, inhibiting erythema, improving skin wrinkles, and/or alleviating skin photoaging.

One or more embodiments provide a health functional food composition having an effect of enhancing skin moisturizing, exfoliating skin, enhancing skin elasticity, inhibiting erythema, improving skin wrinkles, and/or alleviating skin photoaging.

One or more embodiments provide a pharmaceutical or quasi-drug composition having an effect of enhancing skin moisturizing, exfoliating skin, enhancing skin elasticity, inhibiting erythema, improving skin wrinkles, and/or alleviating skin photoaging.

Additional aspects will be set forth in part in the description which follows and, in part, will be apparent from the description, or may be learned by practice of the presented embodiments.

According to an aspect of an embodiment, there is provided a cosmetic composition including ionone or a cosmetically acceptable salt thereof as an active ingredient and having an effect of enhancing skin moisturizing, exfoliating skin, improving skin elasticity, inhibiting erythema, improving skin wrinkles, or alleviating skin photoaging.

According to an aspect of another embodiment, there is provided a health functional food composition including ionone or a sitologically acceptable salt thereof as an active ingredient and having an effect of enhancing skin moisturizing, exfoliating skin, improving skin elasticity, inhibiting erythema, improving skin wrinkles, or alleviating skin photoaging.

In one exemplary embodiment, an amount of the ionone or the cosmetically acceptable salt thereof ranges from about 0.0001 wt % to about 20 wt % with respect to a total weight of the cosmetic composition.

In another exemplary embodiment, the cosmetic composition is prepared in any one formulation selected from the group consisting of a skin lotion, a skin softener, a skin toner, an astringent, a lotion, a milk lotion, a moisturizing lotion, a nutrition lotion, a massage cream, a nutrition cream, a moisturizing cream, a hand cream, an essence, a pack, a mask pack, a mask sheet, an exfoliating agent, a soap, a shampoo, a cleansing foam, a cleansing lotion, a cleansing cream, a body lotion, a body cleanser, an emulsion, a press powder, a loose powder, and an eye shadow.

In another exemplary embodiment, the health functional food composition is prepared in any one formulation selected from the group consisting of tablets, granules, powder, capsules, a liquid solution, and pills.

In another exemplary embodiment, the cosmetic composition or the health functional food composition may further include a skin wrinkle improving ingredient.

In another exemplary embodiment, the skin wrinkle improving ingredient includes one or more selected from the group consisting of vitamin C, retinoic acid, a transforming growth factor (TGF), an animal placenta-derived protein, betulinic acid, and a chlorella extract.

According to an aspect of another embodiment, there is provided a pharmaceutical or quasi-drug composition including ionone or a salt thereof as an active ingredient and having an effect of enhancing skin moisturizing, exfoliating skin, improving skin elasticity, inhibiting erythema, improving skin wrinkles, or alleviating skin photoaging.

According to an aspect of another embodiment, there is provided a method of enhancing skin moisturizing, exfoliating skin, improving skin elasticity, inhibiting erythema, improving skin wrinkles, and/or alleviating skin photoaging, the method including administering a composition including ionone or a pharmaceutically acceptable salt thereof as an active ingredient.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
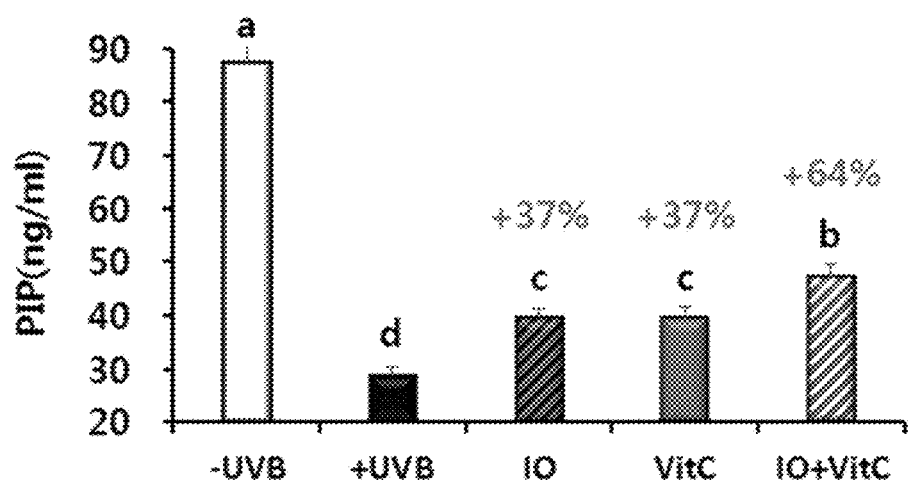
FIG. 1 is a graph showing enzyme-linked immunosorbent assay (ELISA) measurement results of secretion amounts of procollagen of human skin fibroblasts after being irradiated with ultraviolet B (UVB) at a dose of 20 mJ/cm$^2$ and then treated with 100 µM vitamin C or α-ionone (−UVB: a normal group not treated with UVB, +UVB: a control treated with UVB, IO: an experimental group irradiated with UVB and then treated with α-ionone, VitC: a control irradiated with UVB and then treated with vitamin C, and IO+VitC: an experimental group irradiated with UVB and then treated with α-ionone and vitamin C in combination)

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the invention.

Hereinafter, the present disclosure will be described in more detail.

As described above, ionone has been reported to have a strong antimicrobial activity against microorganisms harmful to the human body, but no other physiological activity thereof has been reported.

Under these circumstances, the inventors of the present disclosure verified a novel activity of ionone related to skin health and developed a cosmetic composition, a health functional food composition, a pharmaceutical composition, and a quasi-drug composition that include ionone or a salt thereof as an active ingredient.

The composition according to the present disclosure has a strong activity of enhancing skin moisture content, reducing skin moisture evaporation, increasing procollagen secretion, promoting collagen biosynthesis, inhibiting collagen fiber damage, inhibiting collagen fiber decomposition, inhibiting erythema, and suppressing the thickening of skin epidermis layers, and thus may be usefully used to enhance skin moisturizing, exfoliate skin, enhance skin elasticity, inhibit erythema, reduce skin wrinkles, and/or alleviate skin photoaging.

Accordingly, the present disclosure provides a cosmetic composition including ionone or a cosmetically acceptable salt thereof as an active ingredient and having an effect of enhancing skin moisturizing, exfoliating skin, enhancing skin elasticity, inhibiting erythema, improving skin wrinkles, and/or alleviating skin photoaging.

Ionone is a ketone-based compound having a structural formula of $C_{13}H_{20}O$ and a molecular weight of 192.3 g/mol. Ionone has a total of three isomers and is classified into α-ionone, β-ionone, and γ-ionone represented by Formulae 1, 2, and 3 below, respectively according to molecular structure thereof. α-ionone is also referred to by different names such as (3E)-4-(2,6,6-trimethylcyclohex-2-en-1-yl)but-3-en-2-one, cyclocitrylideneacetone, irisone, jonon, or the like. α-ionone is a pale yellow transparent liquid component having a melting point of −49° C. and a boiling point of about 126° C. to about 128° C.

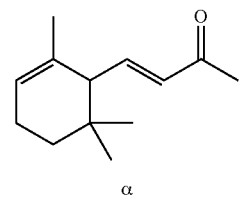

<Formula 1>

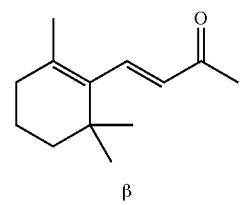

<Formula 2>

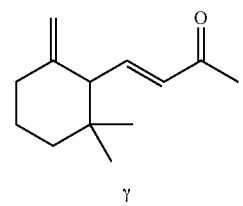

<Formula 3>

Ionone is a fragrance ingredient mainly contained in *Rubus idaeus* (Raspberry), *Daucus carota* subsp. *Sativus* (Carrot), *Prunus dulcis* (Almond), and *Menta* (Herb) and mainly produces the scent of flowers.

A method of obtaining ionone of the present disclosure is not particularly limited. For example, ionone may be isolated from a plant containing the ionone, ionone synthesized chemically using a known preparation method or commercially available ionone may be used.

Ionone has an acceptable daily intake (ADI) value of about 0 mg/kg to about 0.1 mg/kg (JECFA, Safety evaluation of certain food additives. WHO Food Additive Series 42: 335-352, 1999), a $LD_{50}$ value of 2 g/kg body weight, and a maximum daily skin exposure of about 0.0002 mg/kg/day to about 0.331 mg/kg/day (Cadby et al, Consumer exposure to fragrance ingredients: providing estimates for safety evaluation, Regulatory Toxicology and Pharmacology 36: 246-252, 2002).

In addition, it has been reported that, when 32 rats were orally administered 10 mg/day of ionone for 8 weeks, no toxicity was shown (Sporn et al, The effect of certain chemical compounds used in the food industry on the enzymatic activity of the liver, Studii Cercetari Biochim, 7: 23-34, 1964). In another study, it has been reported that, when 72 rats were orally administered 3 mg/mouse of ionone dissolved in oil for 7 weeks every two days, no toxicity was shown (Sporn et al, The toxicity of butyl acetate, methyl naphthyl ketone and ionone, Igiena 12: 437-445, 1963).

Accordingly, ionone may be administered in an amount of about 0.0002 mg/kg to about 1,500 mg/kg, for example, about 0.1 mg/kg to about 1,000 mg/kg so as to have little or no toxicity, and thus may be used in a cosmetic composition, a health functional food composition, a pharmaceutical or quasi-drug composition, and the like at an appropriate concentration within the above-described concentration ranges according to administration method and administration purpose.

In the present disclosure, the ionone may include α-ionone, β-ionone, or γ-ionone without limitation, and may include, within a range having the same efficacy as that of the ionone, an ionone hydrate, an ionone derivative, or the like and may also include a solvate or stereoisomer thereof.

The expression "improving skin wrinkles" as used herein refers to maintaining or strengthening the ability related to wrinkles and elasticity of the skin. Collagen, which is collagenic fiber of the skin dermis layer, and elastin, which is elastic fiber, are the main proteins playing such roles and involved in skin elasticity, and the biosynthesis of collagen is affected by environments inside and outside the skin. In particular, when the activity of skin cells is reduced due to natural aging, the number of collagen fibers decreases, or, as external factors, reactive oxygen species (ROS) generated by irradiation with an excess amount of ultraviolet light, stress, or the like react with a thiol (—SH) group of a protein to inhibit the activity of an enzyme, or increase the expression of a collagenase, elastase, or the like, thereby increasing skin wrinkles and reducing skin elasticity, resulting in the progression of skin aging.

The terms "a cosmetically acceptable salt", "sitologically acceptable salt", "pharmaceutically acceptable salt", or "a salt thereof" as used herein refer to an acid addition salt formed by a free acid. The acid addition salt may be prepared using a general method, for example, by dissolving a compound in an excess amount of an aqueous acid solution, and precipitating the resulting salt using a water-miscible organic solvent, for example, methanol, ethanol, acetone, or acetonitrile. In another embodiment, the acid addition salt may be prepared by heating a compound and acid or alcohol in water (e.g., glycol monomethyl ether) in the same equimolar amounts, drying the resulting mixture by evaporation, or suction-filtering the precipitated salt.

The free acid may be an inorganic acid or an organic acid. Non-limiting examples of the inorganic acid include hydrochloric acid, phosphoric acid, sulfuric acid, nitric acid, and tartaric acid, and these inorganic acids may be used alone or at least two thereof may be used in combination. Non-limiting examples of the organic acid include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, and hydroiodic acid. These organic acids may be used alone or at least two thereof may be used in combination.

In addition, the ionone may be used to prepare a cosmetically or sitologically acceptable metal salt using a base. An alkali metal or alkali earth metal salt may be obtained, for example, by dissolving a compound in an excess amount of an alkali metal hydroxide or alkali earth metal hydroxide solution, filtering the non-soluble compound salt, and then evaporating and drying the filtrate. As the metal salt, in particular, a sodium, potassium or calcium salt may be prepared, but the present disclosure is not limited thereto. In addition, the corresponding silver salt may be obtained by reacting the alkali metal or alkali earth metal salt with an appropriate silver salt (e.g., silver nitrate).

Unless otherwise indicated herein, the salt of the ionone may include all salts of acidic or basic groups which may be present in compounds of the ionone. Non-limiting examples of the salt of the ionone include sodium, calcium and potassium salts of a hydroxyl group, non-limiting examples of other cosmetically acceptable salts of amino groups include hydrobromides, sulfates, hydrogen sulfates, phosphates, hydrogen phosphates, dihydrogen phosphates, acetates, succinate, citrates, tartrates, lactate, mandelate, methanesulfonate (mesylate), and p-toluenesulfonate (tosylate), and these salts may be prepared using a method of preparing a salt, known in the art.

In the cosmetic composition of the present disclosure, an effective amount of the ionone or the cosmetically acceptable salt thereof is not particularly limited, and may range from about 0.0001 wt % to about 20 wt % with respect to a total weight of the cosmetic composition. When the effective amount of the ionone or the cosmetically acceptable salt thereof in the cosmetic composition is less than 0.0001 wt %, the ionone or salt thereof may not exhibit a wrinkle improvement effect due to a very small amount thereof. On the other hand, when the effective amount of the ionone or the cosmetically acceptable salt thereof in the cosmetic composition is greater than 20 wt %, the ionone or salt thereof may exhibit previously known toxicity.

In one embodiment, it was confirmed that, when human skin fibroblasts irradiated with ultraviolet rays were treated with α-ionone, a secretion amount of procollagen type I C-peptide (PIP) was greater than that of a control irradiated with ultraviolet rays alone (see FIG. 1).

Figure 4:
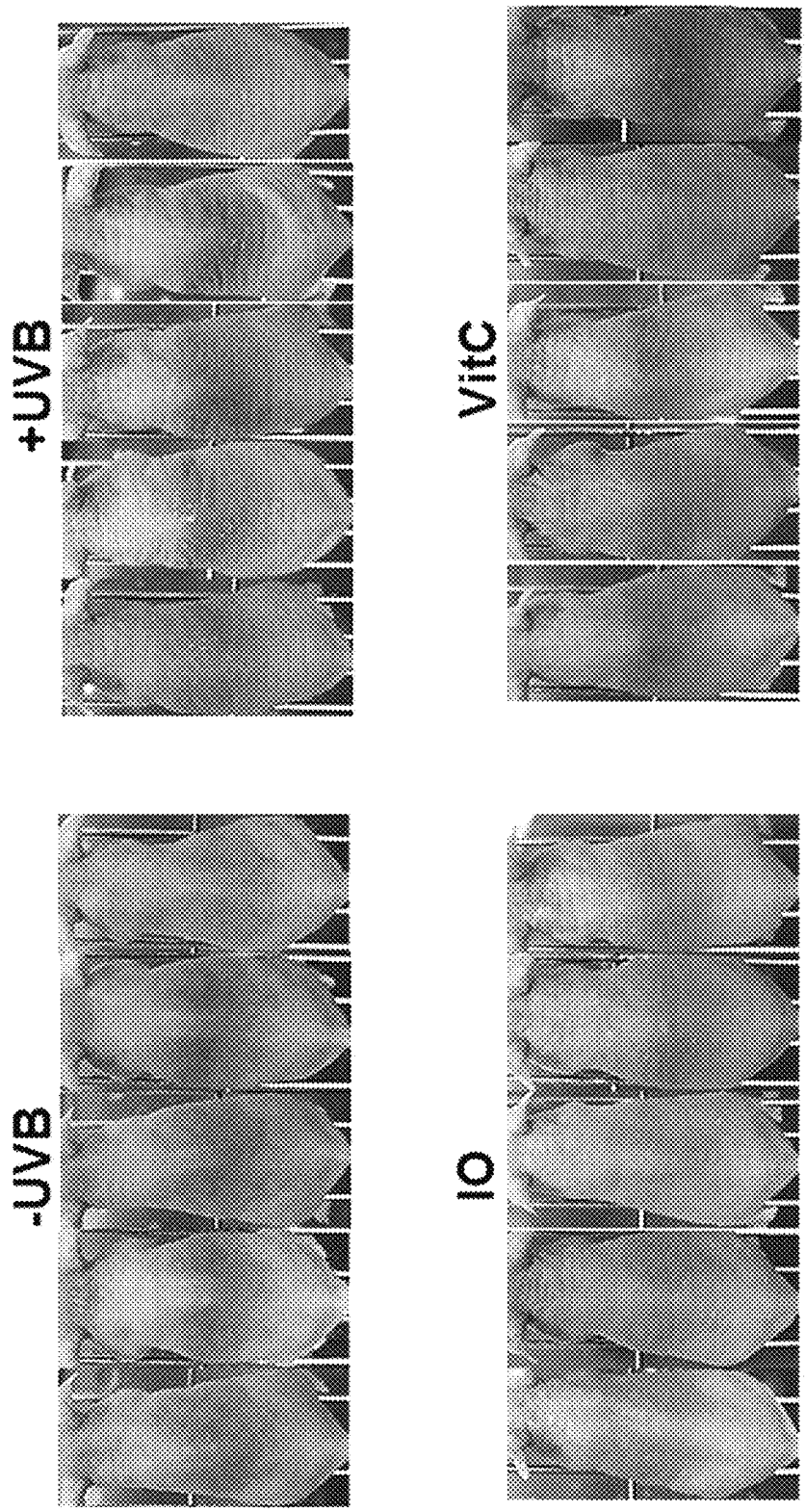
FIG. 4 illustrates images showing dorsal skin tissue of each of the mice fed the experimental diets having the compositions shown in Table 1.
Figure 5A:
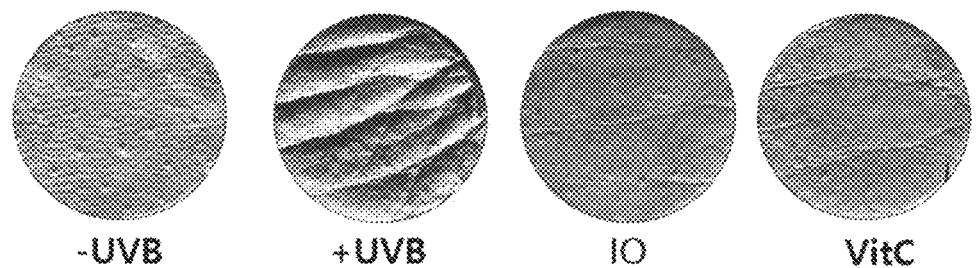
FIGS. 5A-5B respectively illustrate images and graphs showing degrees of wrinkle formation of dorsal skin tissues of the mice fed the experimental diets having the compositions shown in Table 1.
Figure 5B:
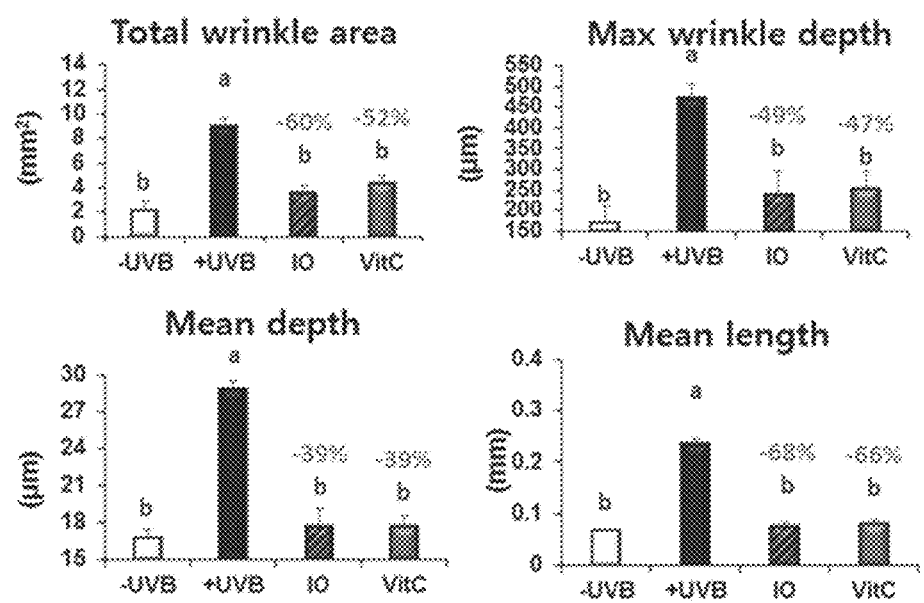
Figure 7:
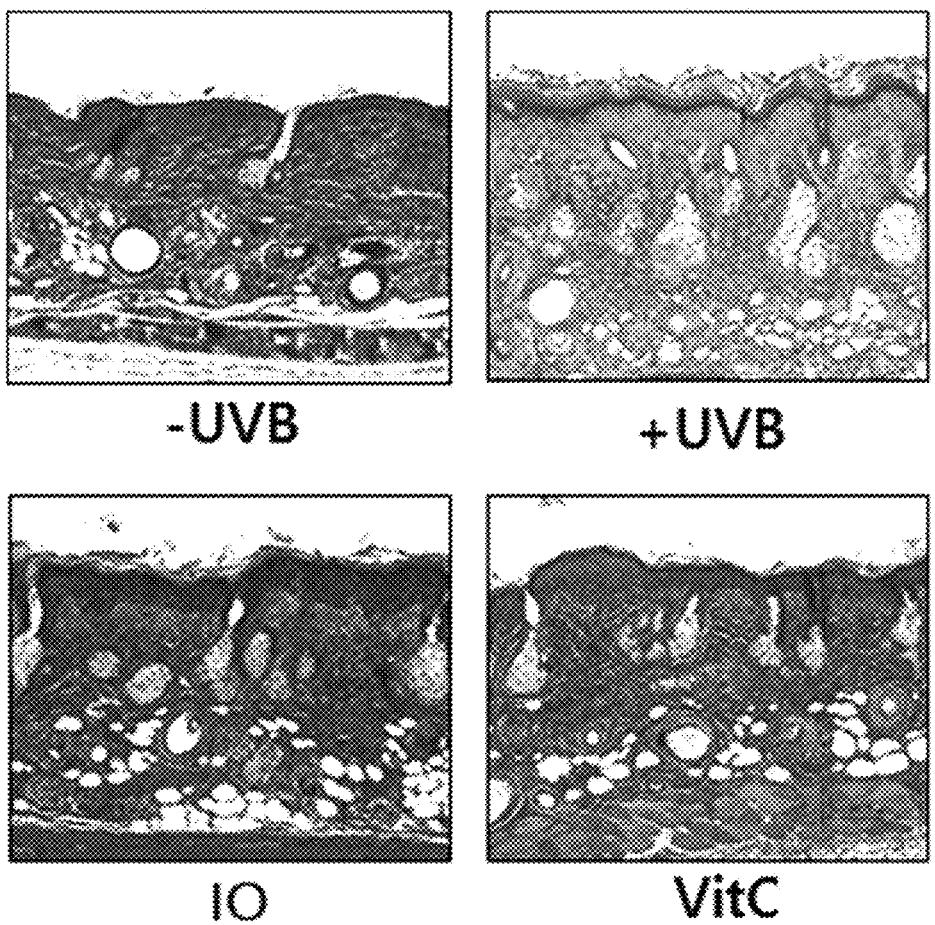
FIG. 7 illustrates images showing quantitative and morphological changes of collagen fibers of the mice fed the experimental diets having the compositions shown in Table 1.
Figure 8:
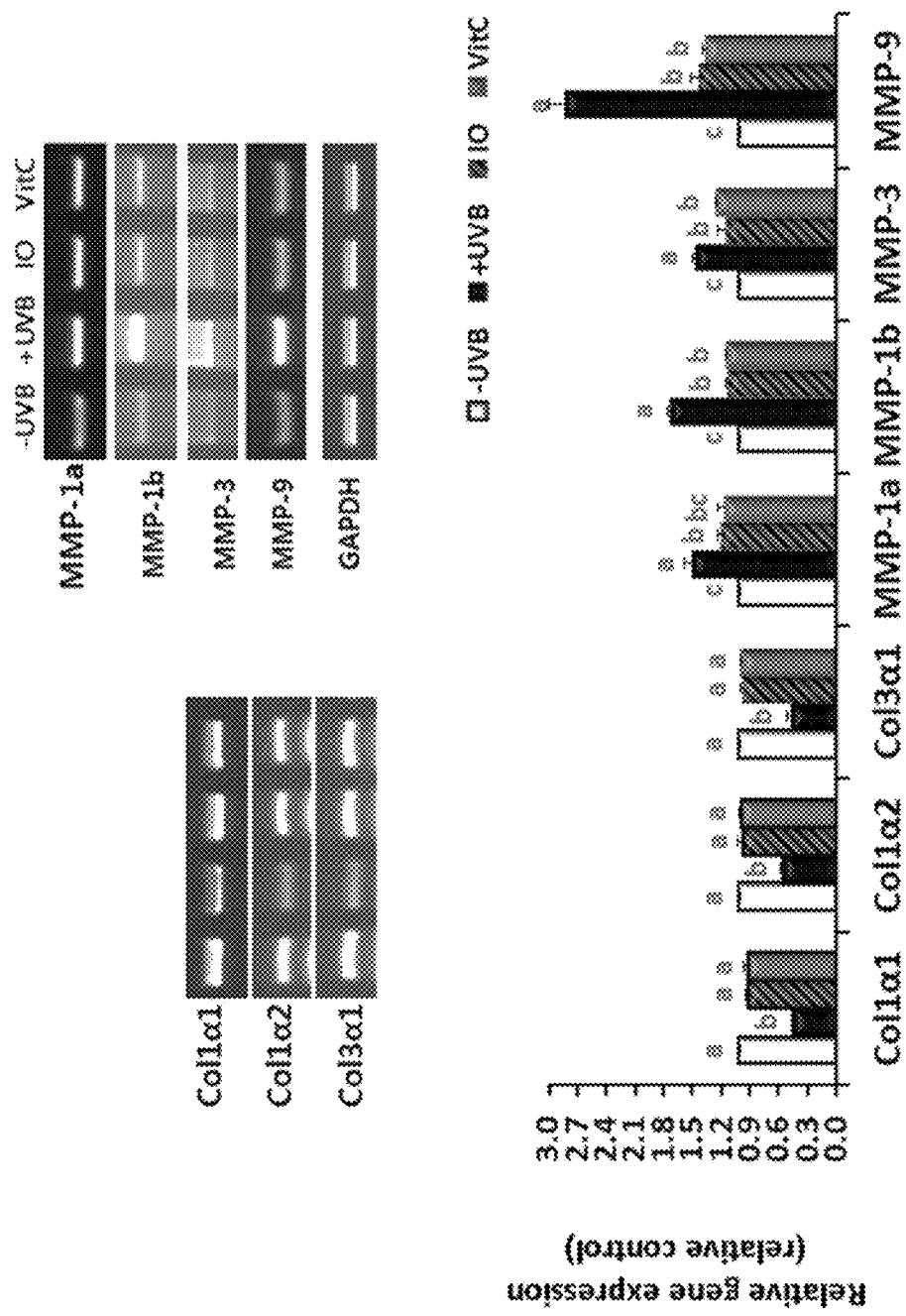
FIG. 8 illustrates reverse transcription polymerase chain reaction (RT-PCR) measurement results of changes in expression of collagen and matrix metalloproteinase (MMP) genes of dorsal tissues of hairless mice treated with α-ionone.

In another embodiment, hairless mice were irradiated with ultraviolet rays and fed experimental diets, containing α-ionone, of Table 1 for 10 weeks, and quantitative and morphological changes in skin moisture content, moisture evaporation, elasticity, the erythema index, wrinkles of dorsal skin tissues, skin thicknesses, and collagenic fibers of the experimental animals and the expression of collagen types 1α1, 1α2, and 3α1 and MMP-1a, MMP-1b, MMP-3 and MMP-9 genes of the skin tissue were measured. As a result, it was confirmed that α-ionone significantly increased the skin moisture content and the elasticity, and significantly reduced the moisture evaporation and the erythema index (see FIG. 3). In addition, it was confirmed that α-ionone improved wrinkles of dorsal skin tissues of the experimental animals (see FIG. 4); had a significant inhibitory effect on the formation of wrinkles by significantly decreasing the area, depth and length of skin wrinkles (see FIG. 5); also significantly decreased the thickness of a thickened epidermis layer (see FIG. 6); had an effect of increasing the density of collagenic fibers and regularly maintaining the arrangement thereof (see FIG. 7); and significantly increased the expression of collagen types 1α1, 1α2, and 3α1 and significantly decreased the expression of MMP-1a, MMP-1b, MMP-3 and MMP-9 genes, thereby increasing the synthesis of collagen proteins and inhibiting decomposition of collagen fibers, resulting in an effective inhibitory effect on the formation of wrinkles due to UV irradiation (see FIG. 8).

Thus, the composition including ionone or a salt thereof according to the present disclosure may be usefully used as a material for a functional cosmetic, a health functional food, a drug, or a quasi-drug, or the like that provides an effect of enhancing skin moisturizing, exfoliating skin, enhancing skin elasticity, improving skin wrinkles, inhibiting erythema, and/or alleviating skin photoaging.

The term "cosmetic composition" as used herein refers to a composition including the compound, having any type of formulation. Non-limiting examples of formulations of cosmetics prepared using the composition include creams such as nutrition creams, eye creams, massage creams, and cleansing creams; packs; lotions such as nutrition lotion; essences; tonics such as skin softeners and nutrition tonics; powders; foundations, and makeup bases. To achieve the technical goal of the present disclosure, the cosmetic composition may be prepared in any formulation selected from the above-listed formulations to be commercialized, and the present disclosure is not limited to the above examples. In addition, the cosmetic composition according to the present disclosure may be formulated using a general cosmetic preparation method.

In particular, the cosmetic composition of the present disclosure may have any one formulation selected from the group consisting of a skin lotion, a skin softener, a skin toner, an astringent, a lotion, a milk lotion, a moisturizing lotion, a nutrition lotion, a massage cream, a nutrition cream, a moisturizing cream, a hand cream, an essence, a pack, a mask pack, a mask sheet, an exfoliating agent, a soap, a shampoo, a cleansing foam, a cleansing lotion, a cleansing cream, a body lotion, a body cleanser, an emulsion, a press powder, a loose powder, and an eye shadow.

The cosmetic composition of the present disclosure may further include, in addition to the ionone or the salt thereof, other additives such as an excipient, a carrier, and the like, and general ingredients added to general skin cosmetics may be applied to the cosmetic composition and mixed therewith in a needed amount.

In particular, the cosmetic composition of the present disclosure may further include a transdermal penetration enhancer. The term "transdermal penetration enhancer" as used herein refers to a composition that allows a desired component to permeate vascular cells of the skin at a high absorption rate. Non-limiting examples of the transdermal penetration enhancer may include other phospholipid components, liposomal components, and the like used in lecithin cosmetics.

In addition, oil that may be mainly used as an oil component may be at least one selected from vegetable oil, mineral oil, silicone oil, and synthetic oil. More particularly, mineral oil, cyclomethicone, squalane, octyldodecyl myristate, olive oil, *Vitis vinifera* seed oil, macadamia nut oil, glyceryl octanoate, castor oil, ethylhexyl isononanoate, dimethicone, cyclopentasiloxane, sunflower seed oil, and the like may be used.

In addition, to reinforce the emulsifying ability, about 0.1 wt % to about 5 wt % of a surfactant, a higher alcohol, or the like may be added. The surfactant may be a general surfactant such as a nonionic surfactant, an anionic surfactant, a cationic surfactant, an amphoteric surfactant, a phospholipid, or the like, and may be, for example, sorbitan sesquinoleate, polysorbate 60, glyceryl stearate, lipophilic glyceryl stearate, sorbitan oleate, sorbitan stearate, diacetyl phosphate, sorbitan stearate/sucrose cocoate, glyceryl stearate/polyethylene glycol-100 stearate, ceteareth-6 olivate, arachidyl alcohol/behenyl alcohol/arachidyl gluco side, polypropylene glycol-26-butes-26/polyethylene glycol-40 hydrogenated castor oil, or the like. The higher alcohol may be a $C_{12}$ to $C_{20}$ alcohol, for example, cetyl alcohol, stearyl alcohol, octyldodecanol, isostearyl alcohol, or the like, and these higher alcohols may be used alone or at least two thereof may be used in combination.

To adjust the viscosity or hardness of a water-phase component, about 0.001 wt % to about 5 wt % of at least one thickening agent selected from carbomer, xanthan gum, bentonite, magnesium aluminum silicate, cellulose gum, dextrin palmitate, and the like may further be added.

In addition, the cosmetic composition according to the present disclosure may further include, according to need, components, for example, a medicinal ingredient such as higher fatty acids, vitamins, or the like; a UV screening agent; an antioxidant (butylhydroxyanisole, gallic acid propyl, erythorbic acid, tocopheryl acetate, butylated hydroxytoluene, or the like); a preservative (methylparaben, butylparaben, propylparaben, phenoxyethanol, imidazolidinyl urea, chlorphenethine, or the like); a colorant, a pH adjusting agent (triethanolamine, citric acid, sodium citrate, malic acid, sodium malate, fumaric acid, sodium fumarate, succinic acid, sodium succinate, sodium hydroxide, sodium monohydrogen phosphate, or the like); a moisturizing agent (glycerin, sorbitol, propylene glycol, butylene glycol, hexylene glycol, diglycerin, betaine, glycereth-26, methyl gluceth-20, or the like); a lubricant; and the like.

In addition, the cosmetic composition of the present disclosure may further include an adjuvant for supplying an essential nutrient to the skin, for example, an adjuvant with natural flavor or cosmetic flavor, or medicinal herbs, but may include any adjuvant without being limited to these examples.

In addition, the cosmetic composition of the present disclosure may further include a skin wrinkle improving ingredient or a skin elasticity enhancing ingredient. For example, the skin wrinkle improving ingredient or the skin elasticity enhancing ingredient may be at least one selected from the group consisting of vitamin C, retinoic acid, a TGF, an animal placenta-derived protein, betulinic acid, and a chlorella extract. For example, the skin wrinkle improving ingredient or the skin elasticity enhancing ingredient may be most preferably vitamin C.

In one embodiment, it was confirmed that, when human skin fibroblasts irradiated with ultraviolet rays were treated with α-ionone and vitamin C in combination, the amount of collagen measured was larger than in a case of being treated with α-ionone or vitamin C alone, which indicates a synergistic effect (see FIG. 1).

The present disclosure also provides a health functional food composition including ionone or a sitologically acceptable salt thereof as an active ingredient and having an effect of enhancing skin moisturizing, exfoliating skin, improving skin elasticity, inhibiting erythema, improving skin wrinkles, and/or alleviating skin photoaging.

The description of the terms "ionone" and "sitologically acceptable salt thereof" as used herein has already been provided.

The term "health functional food" as used herein refers to foods prepared and processed in the form of tablets, capsules, powder, granules, a liquid, pills, or the like by using raw materials or ingredients having useful functionality in the human body. The term "functionality" as used herein refers to controlling nutrients for the structure of functions of the human body or providing useful effects of hygienic purposes, such as psychological effects, and the like. The health function food of the present disclosure may be prepared using a method commonly used in the art, and may be prepared by adding raw materials and ingredients commonly added in the art. In addition, the formulation of the health function food is not particularly limited so long as it is recognized as a health functional food. The health functional food composition of the present disclosure uses a food as a raw material unlike generic drugs, and thus has no side effects that may occur during long-term administration thereof, is highly portable, and may be administered as an adjuvant for enhancing skin moisturizing, exfoliating skin, improving skin elasticity, inhibiting erythema, improving skin wrinkles, and/or alleviating skin photoaging.

The food functional food composition of the present disclosure may be prepared in any one formation selected from the group consisting of tablets, granules, powder, capsules, a liquid solution, and pills.

The health functional food composition according to the present disclosure may be formulated in the form of powder, a liquid, tablets, soft capsules, granules, a tea bag, an instant tea, a drink, or the like by including ionone as an active ingredient. The amount of ionone as an active ingredient may be appropriately determined according to the purpose of use (for prevention or improvement). In general, the amount of ionone included in a health functional food composition may range from about 0.1 wt % to about 90 wt % based on a total weight of the food. However, in the case of long-term administration for health and hygiene purposes or for the purpose of controlling health, the amount may be less than the above-described range. In addition, the health functional food composition according to the present disclosure may further include, in addition to ionone, other ingredients that may impart a synergistic effect to main effects within a range that does not impair desired main effects, for example, a wrinkle improving compound such as vitamin C, or a natural substance such as a green tea extract, an extract of the paper mulberry, a licorice extract, a mulberry root extract, a betel nut extract, a golden extract, a wild ginseng extract, or the like.

The health functional food composition formulated in the above-described form may be directly added to a food or may be used in combination with other foods or food ingredients, and may be appropriately used according to a general method. Non-limiting examples of suitable foods include drinks, meats, sausages, bread, biscuits, rice cakes, chocolates, candies, snacks, confectionaries, pizzas, instant noodles, other noodles, gums, dairy products including ice creams, various kinds of soup, beverages, alcoholic drinks, vitamin complexes, and milk and dairy products, and all health functional foods in the ordinary sense are included.

When the health functional food composition of the present disclosure is a drink, the drink includes ionone as an essential ingredient in the indicated ratio, and other ingredients used for the preparation of drinks are not particularly limited, and the drink may further include various flavoring agents, natural carbohydrates, or the like as in general beverages. Examples of the natural carbohydrates include general sugars, for example, monosaccharides such as glucose, fructose, and the like; disaccharides such as maltose, sucrose, and the like; and polysaccharides such as dextrin, cyclodextrin, and the like, and sugar alcohols such as xylitol, sorbitol, erythritol, and the like. Natural flavoring agents, synthetic flavoring agents, and the like may be used as a flavoring agent in addition to the above-described flavoring agents. The amount of the natural carbohydrate may generally range from about 1 g to about 20 g, for example, about 5 g to about 12 g based on 100 ml of the composition of the present disclosure.

In addition, the health functional food composition of the present disclosure may include various nutrition supplements, a vitamin, a mineral (electrolyte), a flavoring agent such as a synthetic flavoring agent, a natural flavoring agent, or the like, a colorant, a thickening agent such as cheese, chocolate, or the like, pectic acid and a salt thereof, alginic acid and a salt thereof, an organic acid, a protective colloid thickening agent, a pH adjusting agent, a stabilizer, a preservative, glycerin, an alcohol, a carbonating agent used in carbonated drinks, or the like. In addition thereto, the food composition of the present disclosure may include flesh for the preparation of natural fruit juice, fruit juice drinks, and vegetable drinks. These ingredients may be used alone or in combination. The proportion of these additives is not so critical, but may generally range from about 0.1 parts by weight to about 20 parts by weight based on 100 parts by weight of the ionone of the present disclosure.

The present disclosure also provides a pharmaceutical or quasi-drug composition including ionone or a salt thereof as an active ingredient and having an effect of enhancing skin moisturizing, exfoliating skin, enhancing skin elasticity, inhibiting erythema, improving skin wrinkles, and/or alleviating skin photoaging.

The description of the terms "ionone" and "salt thereof" as used herein has already been provided.

When the ionone or the pharmaceutically acceptable salt thereof is used as a pharmaceutical, it may further include one or more active ingredients exhibiting the same or similar functions. For example, the pharmaceutical may include a known skin wrinkle improving ingredient or elasticity enhancing ingredient. When the pharmaceutical further includes such a skin wrinkle improving ingredient and an elasticity enhancing ingredient, wrinkle and elasticity improving effects of the composition of the present disclosure may further be increased. At the time of adding above-described ingredients, skin safety, easiness of formulation, and stability of active ingredients according to combined use thereof may be considered. In one embodiment, the pharmaceutical composition may further include at least one known skin wrinkle improving ingredient selected from the group consisting of vitamin C, retinoic acid, a TGF, an animal placenta-derived protein, betulinic acid, and a chlorella extract. The amount of the additional skin wrinkle improving ingredient may range from about 0.0001 wt % to about 10 wt % with respect to a total weight of the composition. The amount range may be adjusted according to requirements such as collagen synthesis promoting activity, skin safety, easiness during formulation of a compound represented by Formula 1 below, and the like.

In addition, a pharmaceutical composition for improving skin wrinkles and enhancing skin elasticity, according to the present disclosure, may further include a pharmaceutically acceptable carrier.

The pharmaceutically acceptable carrier may include various components, such as a buffer, injectable sterile water, normal saline or phosphate buffered saline, sucrose, histidine, salts, polysorbates, and the like.

The pharmaceutical composition of the present disclosure may be administered orally or parenterally, and may be administered in various formulations for oral and parenteral administration upon clinical administration. The pharmaceutical composition may be formulated using a generally used diluent or excipient such as a filler, an extender, a binder, a wetting agent, a disintegrant, a surfactant, or the like.

Non-limiting examples of solid preparations for oral administration include tablets, pills, powder, granules, and capsules. Such solid preparations may be formulated in combination with at least one excipient, for example, starch, calcium carbonate, sucrose, lactose, gelatin, or the like.

In addition to simple excipients, lubricants such as magnesium stearate and talc may also be used. Non-limiting examples of liquid preparations for oral use include suspensions, solutions, emulsions, and syrups. In addition to commonly used simple diluents such as water and liquid paraffin, various excipients, for example, a wetting agent, a sweetening agent, a fragrance, a preservative, and the like may be included.

Examples of formulations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, a vegetable oil such as olive oil, and an injectable ester such as ethyl oleate. Examples of suppository bases include Witepsol, Macrogol, Tween 61, cacao butter, laurin, glycerogelatin, and the like.

When the pharmaceutical composition of the present disclosure includes an effective amount of ionone or a pharmaceutically acceptable salt thereof, it may provide an effect of enhancing skin moisturizing, exfoliating skin, improving skin elasticity, inhibiting erythema, improving skin wrinkles, and/or alleviating skin photoaging. The term "effective amount" as used herein refers to the amount of a compound capable of preventing or inhibiting the generation of skin wrinkles, or alleviating already formed wrinkles. The effective amount of ionone or a pharmaceutically acceptable salt thereof included in the composition of the present disclosure may vary depending on a prepared type of the composition, a method of applying the compound to the skin, time maintained on the skin, and the like. For example, when the composition is prepared into a drug for dermatological treatment due to the formation of skin wrinkles, reduced elasticity, freckles, and the like, the prepared composition may include ionone or a pharmaceutically acceptable salt thereof at a higher concentration than when prepared into a cosmetic commonly applied to the skin.

The term "quasi-drug" as used herein refers to products that are less effective than pharmaceuticals, among products used for diagnosing, curing, improving, alleviating, treating, or preventing diseases of humans or animals. For example, according to the Pharmaceutical Affairs Law, quasi-drugs exclude products used as pharmaceuticals, and include products used for curing or preventing diseases of humans and animals, products which minimally act on the human body or do not act directly on the human skin, and the like.

The quasi-drug composition of the present disclosure is used for enhancing skin moisturizing, exfoliating skin, improving skin elasticity, inhibiting erythema, improving skin wrinkles, and/or alleviating skin photoaging, and formulations thereof are not particularly limited. For example, the quasi-drug composition may be a cosmetic composition in any formulation of a softening lotion, a nutrition lotion, a massage cream, a nutrition cream, a pack, a mask pack, a mask sheet, or a gel- or a skin adhesive-type cosmetic, and may also be in any formulation for dermal administration, such as a lotion, an ointment, a gel, a cream, a patch, or a spraying agent.

In addition, the quasi-drug composition in each formulation may be mixed with other ingredients arbitrarily selected according to formulations of other quasi-drugs, the purpose of use, or the like. A mixing amount of the active ingredient may be suitably determined according to the purpose of use (inhibition or alleviation). For example, the active ingredient may include general adjuvants such as a thickener, a stabilizer, a solubilizer, a pigment, and a flavoring, a carrier, and the like.

The amount of the ionone or the salt thereof of the present disclosure may range from about 0.0001 wt % to about 20 wt % based on a total weight of the quasi-drug composition. When the amount of the ionone or the salt thereof is greater than 20 wt %, color and stability deteriorate when the composition is prepared. When the amount of the ionone or the salt thereof is less than 0.0001%, the action and effect thereof are insignificant.

In addition, in the quasi-drug composition of each formulation, other ingredients in addition to the above-described essential ingredients may be appropriately selected and mixed by one of ordinary skill in the art without undue difficulty according to formulation, the purpose of use, and the like.

Hereinafter, the present disclosure will be described in further detail with reference to the following examples. It will be obvious to those of ordinary skill in the art that these examples are provided only for illustrative purposes and are not intended to limit the scope of the present disclosure.

Example 1

Wrinkle Improving Efficacy of α-Ionone Using Human Skin Fibroblasts 1-1. Experimental Method 1) Cell Culture Primary dermal fibroblasts (normal, human, neonatal, ATCC No. PCS-201-010) were purchased from ATCC (Manassas, Va., USA). The purchased cells were incubated in a 5% $CO_2$ incubator at 37° C. by using a fibroblast growth medium (Promo Cell, Heidelberg) and used in experiments.

2) Procollagen Type IC-Peptide (PIP) Concentration Measurement

To examine collagen biosynthesis ability, human fibroblasts were distributed into a 12 well-plate at a concentration of $1.0 \times 10^6$ cells/well, α-ionone and vitamin C were added thereto at a concentration of 100 μM each, and the resulting human fibroblasts were incubated in a $CO_2$ incubator for 24 hours. After removing the medium from each well, the plate was washed once with PBS, and 1 ml of PBS was added thereto, followed by irradiation with ultraviolet B (UVB) at a dose of 20 mJ/cm². The PBS of each well was replaced by a medium and the human fibroblasts were cultured for 24 hours, and then the amount of procollagen secreted into the medium was measured using a procollagen type C-peptide EIA kit (Takara Bio, Japan). A standard solution included in the collagen measurement kit was diluted according to concentration, absorbance was measured at 450 nm to create a standard concentration curve, and the amount of collagen produced was calculated.

1-2. Experimental Results

1) Changes in Secretion Amount of Procollagen

Collagen, which is the main protein that makes up the skin, is synthesized in the form of procollagen in fibroblasts present in the skin dermis and then secreted into the extracellular matrix. The C-terminal of procollagen secreted into the extracellular matrix is cleaved by procollagen peptidase present on cell surfaces and formed into active collagen, and thus the amount of the active collagen may be measured by measuring the amount of C-peptide. Each value of FIG. 1 denotes mean±SEM of three measurements from three independent wells. The mean value for the different letters indicates statistical significance ($p<0.05$).

Human skin fibroblasts were irradiated with ultraviolet rays and treated with a drug and then amounts of procollagen secreted into the extracellular matrix and procollagen type I C-peptide (PIP) were measured. As a result, control cells irradiated with ultraviolet rays alone (+UVB) exhibited a significantly decreased secretion amount of procollagen compared to that of normal cells (−UVB), and cells (10) irradiated with ultraviolet rays and treated with α-ionone exhibited a significant increase of 37% in the amount of collagen, compared to the control cells irradiated with ultraviolet rays alone (+UVB). Meanwhile, cells (IO+VitC) treated with α-ionone and vitamin C in combination exhibited a significant increase of 64% in the amount of collagen, compared to the control cells irradiated with ultraviolet rays alone (+UVB), which is much greater than the amount of collagen observed in cells treated with vitamin C (+37%) alone or α-ionone (+37%) alone (see FIG. 1). When these results are substituted into Colby's equation, it can be confirmed that, when α-ionone and vitamin C are treated in combination, a synergistic effect is shown. Thus, it can be confirmed that α-ionone increases the amount of collagen activated in human skin fibroblasts and such a collagen increasing effect is more effective when used together with vitamin C.

Example 2

Evaluation of Efficacy of α-Ionone on Improving Skin Wrinkles and Enhancing Skin Moisturizing and Elasticity Using Mice 2-1. Experimental Method 1) Preparation of Experimental Diets, Experimental Animal Rearing, and Ultraviolet Irradiation 5-week-old female albino hairless mice (Skh-1) used in the present example were purchased from ORIENTBIO (Gyeonggi-do, Korea) and subjected to an adaptation period of 1 week with solid feed. The experimental animal was divided into 4 groups and 5 mice were assigned to each group. All the experimental groups were divided into a normal control not irradiated with ultraviolet rays (−UVB), a group irradiated with ultraviolet rays (+UVB), and a group irradiated with ultraviolet rays and treated with α-ionone (αIO) or vitamin C (VitC). During a rearing period, the experimental groups were freely fed feed and water, temperature and humidity were maintained at 22±1° C. and 60±5%, a light period and a dark period were adjusted every day to 12 hours.

The −UVB and +UVB groups were fed a purified diet formulated based on the AIN-93 rodent diet composition (Ree yes, P G et al., J Nutr, 123:1939-1951, 1993) for 10 weeks, the αIO group were fed an AIN-93 purified diet with 0.2% of α-ionone (Sigma-Aldrich) for 10 weeks, and the VitC group was fed a diet, prepared by adding 0.2% of vitamin C (Sigma-Aldrich) to the AIN-93 purified diet, for 10 weeks. Detailed compositions of the experimental diets are shown in Table 1 below. The diets were supplied daily with water between 10 am and 11 am, and food intakes were measured daily.

TABLE 1

Experimental diet composition table

| Ingredient | AIN-93G diet (g/kg diet) | α-ionone supplemented diet (IO) (g/kg diet) | Vitamin C supplemented diet (VitC) (g/kg diet) |
|---|---|---|---|
| Casein | 200 | 200 | 200 |
| Maltodextrin | 132 | 132 | 132 |
| Corn starch | 397.486 | 395.486 | 395.486 |
| Sucrose | 100 | 100 | 100 |
| Cellulose | 50 | 50 | 50 |
| Soybean oil | 70 | 70 | 70 |
| Vitamin complexes | 10 | 10 | 10 |
| Mineral complexes | 35 | 35 | 35 |
| Choline bitartrate | 2.5 | 2.5 | 2.5 |
| L-cystine | 3 | 3 | 3 |
| Tert-butyhydroquinone | 0.014 | 0.014 | 0.014 |
| α-ionone | — | 2 | — |
| Vitamin C | — | — | 2 |
| Total (g) | 1,000 | 1,000 | 1,000 |

During the experimental rearing period, dorsal parts of the hairless mice were irradiated with UVB three times a week, and the amount of ultraviolet radiation was 73 mJ/cm$^2$ for the first one week, 146 mJ/cm$^2$ for the second week, and 219 mJ/cm$^2$ for the third week to the tenth week. During rearing, body weights and skin thicknesses of the experimental groups were measured weekly, and images of dorsal skin parts thereof were taken. The skin thicknesses of buttocks of the hairless mice were measured using a digital micro caliper (Marathon Watch Company Ltd, Ontario, Canada). The caliper used in the measurement was able to measure a thickness up to 0.01 mm and had a control function to apply constant force to the thickness, so it was possible to measure skin thicknesses under the same force.

On the last day of the experimental rearing, the experimental animal groups were starved for 6 hours and anesthetized, and blood and dorsal skin tissues thereof were collected. Each blood sample was collected from the abdominal inferior vena cava using a syringe, placed in an EDTA-coated tube, and centrifuged at 2,000×g for 15 minutes, and then plasma was separated therefrom and stored frozen at −70° C. until analysis. Some of the dorsal skin tissues were immediately stored in a freezer at −70° C., and then used for molecular biological assay, and some thereof were fixed in a 10% formalin solution and then used for immunohistochemical staining.

2) Measurement of Skin Moisturization, Elasticity, and Erythema Index

Skin moisture content, moisture evaporation, elasticity, and the erythema index of each of the experimental animal groups were measured once on the last day of the experiment using Corneometer®, Tewameter®, Cutometer®, and Mexameter® (Courage+Khazaka electronic GmbH), respectively. During the measurement, the value obtained by lightly pressing a certain portion of the experimental animal or the like was recorded.

3) Measurement of Wrinkles on Dorsal Skin Tissue

The skin of each hairless mouse irradiated with ultraviolet rays for 10 weeks was replicated using silicone rubber and a degree of the formation of wrinkles was measured. A disk with a circular hole having a diameter of 1 cm was attached to a dorsal part of the hairless mouse, reagents for preparing a replica were mixed, the mixed resultant was thinly spread on the dorsal art of the hairless mouse and completely dried, and then the disk was carefully detached therefrom, thereby completing the preparation of the replica. The replica was prepared at a temperature of about 20° C. to about 23° C. and a humidity of about 45% to about 50% under constant temperature and constant humidity conditions, a silicon rubber impression material (Epigem, Seoul, Korea) for preparing a replica was used. To analyze the prepared replica, four wrinkle indexes, such as a total wrinkle area, a maximum wrinkle depth, a mean depth, and a mean length were analyzed using a computer image analyzer (Visioline VL650, Courage+Khazaka electronic GmbH, Germany).

4) Immunohistochemical Staining of Skin Tissue

Dorsal skin tissues of the hairless mice were extracted and fixed in 10% formalin, and then Hematoxylin and eosin (H&E) and Masson's trichrome (M&T) staining by the Korean CFC (Gyeonggi-do, Korea) was requested, followed by observation with an optical microscope (IX71, Olympus, JPN), and images thereof were taken using a digital camera (DP71, Olympus, JPN).

5) RT-PCR Analysis

The dorsal skin tissue was pulverized by adding 1 ml of a TRIzol solution per 0.1 g of the tissue, and then centrifuged at 12,000×g for 10 minutes at 4° C. The supernatant was transferred to a new tube, and then 200 μl of chloroform was added thereto and vortexed. After this process was repeated twice, the supernatant was transferred to a new tube and then isoprophanol was added thereto at a ratio of 1:1 (isoprophanol:supernatant). The resulting supernatant was strongly shaken 10 times and then maintained at room temperature for 15 minutes, followed by centrifugation at 12,000×g for 10 minutes at 4° C. and removal of the supernatant, 1 ml of 70% ethanol was added to the remaining precipitate and then centrifuged at 7,500×g for 5 minutes at 4° C. After removing ethanol therefrom, a tube containing the RNA precipitate was dried at room temperature for 15 minutes, and the RNA pellet was dissolved using nuclease free water. The concentration of the extracted RNA sample at wavelengths of 260 nm and 280 nm was measured using a UV/VIS spectrophotometer (Beckman Coulter, DU730), and the integrity of the RNA sample was confirmed by agarose gel electrophoresis.

The RNA sample extracted from the dorsal skin tissue was subjected to reverse transcription using an oligo dT primer and superscript reverse transcriptase (GIBCO BRL, Gaithersburg, Md., USA), thereby synthesizing cDNA. PCR was performed using the cDNA obtained through reverse transcription as a template and the 5' and 3' flanking sequences of a cDNA gene to be amplified as a primer. In this regard, the used primer sequence is shown in Table 2 below. 1 μl of the amplified PCR product was electrophoresed on 1% agarose gel to confirm DNA bands.

2-2. Experimental Results

1) Body Weights and Food Intakes of Hairless Mice

Figure 2:
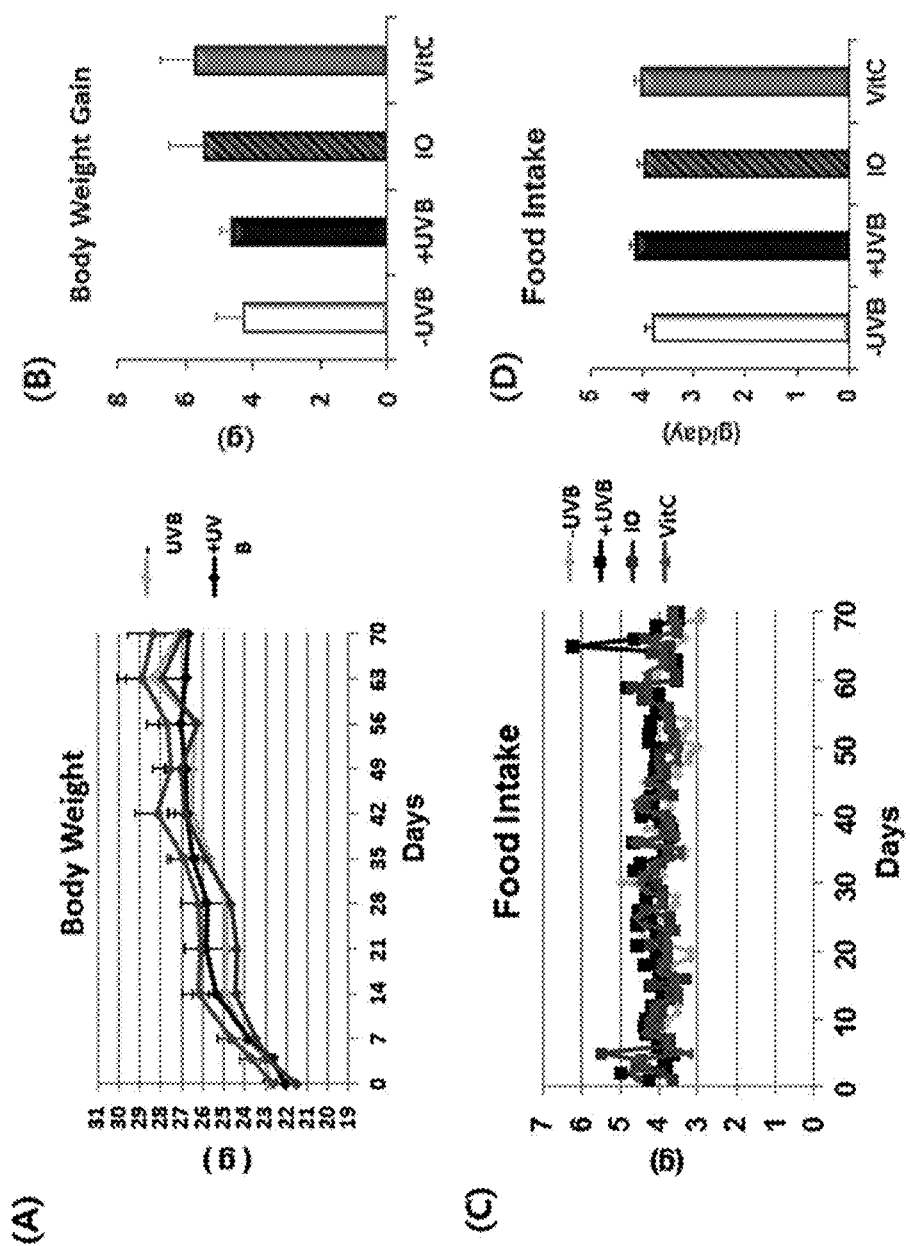
FIG. 2 illustrates graphs showing body weight gains and food intakes of mice fed experimental diets having the compositions shown in Table 1.

UV irradiation, α-ionone, and vitamin C had no significant effect on body weights and food intakes of the hairless mice (see FIG. 2). The values shown in FIG. 2 indicate mean±SEM of five mice.

Figure 3:
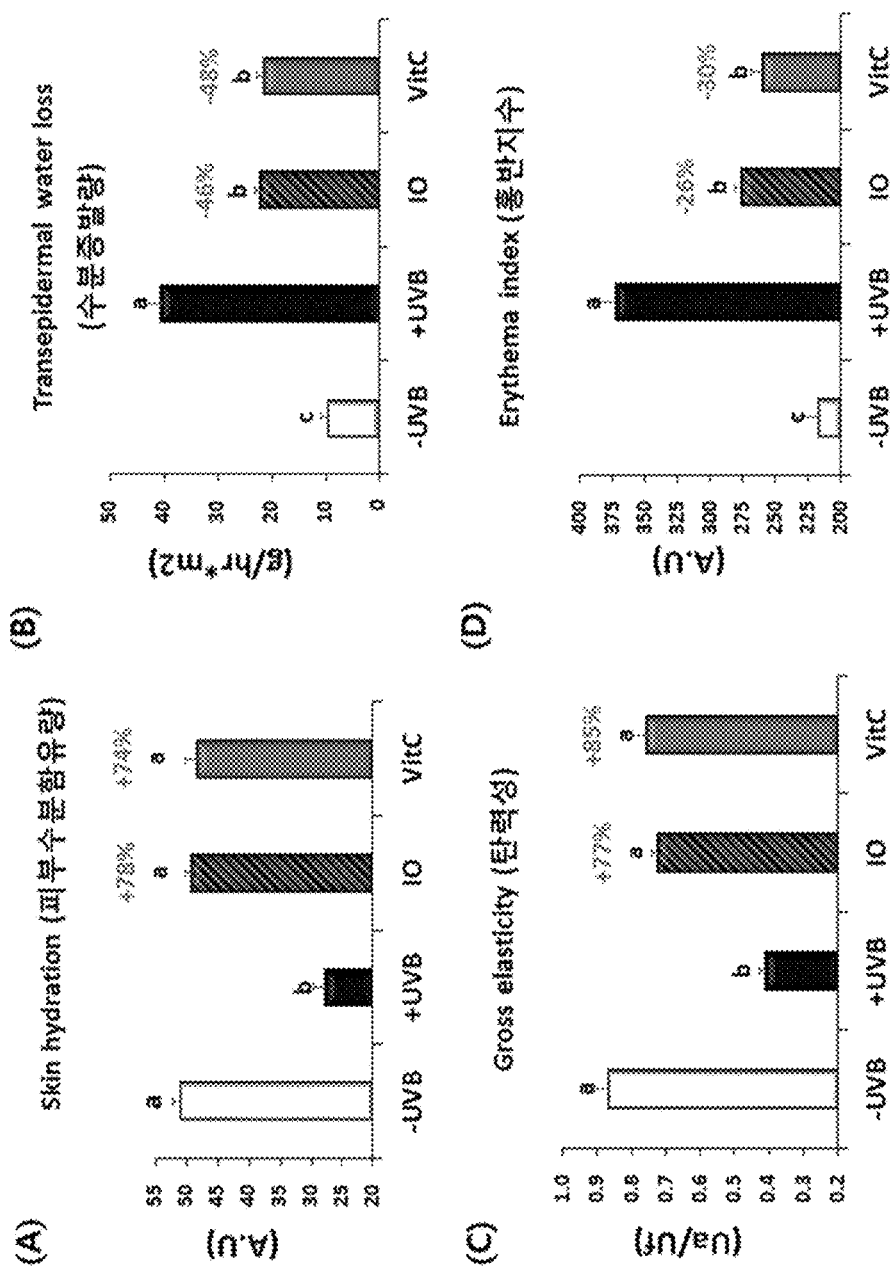
FIG. 3 includes graphs showing skin hydration (A), transepidermal water loss (B), gross elasticity (C), and the erythema index (D) of skin tissues of mice fed the experimental diets having the compositions shown in Table 1.

2) Changes in Moisture Content, Elasticity, and Erythema Index of Skin Tissues of Ultraviolet Rays-Irradiated Hairless Mice The +UVB control irradiated with ultraviolet rays for 10 weeks exhibited a significant decrease in moisture content and elasticity of the skin tissue and a significant increase in moisture evaporation and the erythema index, compared to the normal group (−UVB) not irradiated with ultraviolet rays (see FIG. 3). The group (10) treated with α-ionone exhibited significant increases of 78% and 77% in moisture content and elasticity, respectively, and significant decreases of 46% and 26% in moisture evaporation and the erythema index, respectively, compared to the +UVB control, even though the two groups were irradiated with the same UV intensity. Such efficacy of α-ionone on enhancing moisture content, elasticity, and the erythema index was similar to an effect obtained by vitamin C (see FIG. 3). The values shown in FIG. 3 denote mean±SEM of five mice, and a letter above

TABLE 2

Primer sequences used in RT-PCR

| Gene | Primer | Sequence (5'→3') | Annealing temperature (° C.) | PCR product (bp) |
|---|---|---|---|---|
| Collagen type I alpha1 (Col1α1) | F | ggcaacagtcgcttcaccta (SEQ ID NO: 1) | 55 | 164 |
|  | R | agtccgaattcctggtctgg (SEQ ID NO: 2) |  |  |
| Collagen type I alpha2 (Col1α2) | F | cggttctgttggtcctgttg (SEQ ID NO: 3) | 55 | 103 |
|  | R | acccctgtgccctttatcac (SEQ ID NO: 4) |  |  |
| Collagen type III alpha1 (Col3α1) | F | taaccaaggctgcaagatgg (SEQ ID NO: 5) | 55 | 104 |
|  | R | accagtgcttacgtgggaca (SEQ ID NO: 6) |  |  |
| Matrix metallopeptidase 1a (MMP-1a) | F | ccctgtgtttcacaacggag (SEQ ID NO: 7) | 55 | 133 |
|  | R | cctcagcttttcagccatca (SEQ ID NO: 8) |  |  |
| Matrix metallopeptidase 1b (MMP-1b) | F | tttgctcatgcttttctgcc (SEQ ID NO: 9) | 55 | 146 |
|  | R | gaatgggagagtccaaggga (SEQ ID NO: 10) |  |  |
| Matrix metallopeptidase 3 (MMP-3) | F | tgctggtatggagcttctgc (SEQ ID NO: 11) | 55 | 142 |
|  | R | catctccaacccgaggaact (SEQ ID NO: 12) |  |  |
| Matrix metallopeptidase 9 (MMP-9) | F | gtggaccatgaggtgaacca (SEQ ID NO: 13) | 55 | 102 |
|  | R | actgcacggttgaagcaaag (SEQ ID NO: 14) |  |  |
| Glyceraldehyde 3-phosphate dehydrogenase (GAPDH) | F | ggagattgttgccatcaacg (SEQ ID NO: 15) | 55 | 122 |
|  | R | tgacaagcttcccattctcg (SEQ ID NO: 16) |  |  | each bar indicates significant difference by one-way ANOVA followed by a Duncan's multiple range test ($p<0.05$).

3) Changes in Formation of Skin Wrinkles of Ultraviolet Rays-Irradiated Hairless Mice To evaluate an effect of α-ionone intake on a degree of formation of skin wrinkles, images of the dorsal skin parts of the experimental animal groups were taken. In the case of the +UVB control irradiated with UVB for 10 weeks, a plurality of thick and deep wrinkles and fine wrinkles were observed with the naked eye, compared to the normal group (−UVB) not irradiated with ultraviolet rays, and the group treated with α-ionone exhibited a significant decrease in the thickness and depth of wrinkles, compared to the +UVB control, and thus had a skin condition similar to that observed in the −UVB group not irradiated with ultraviolet rays (see FIG. 4).

The dorsal skin of each hairless mouse irradiated with ultraviolet rays for 10 weeks was replicated using silicone rubber and a degree of formation of wrinkles was measured. As a result, it was confirmed that thick and deep wrinkles and fine wrinkles were observed in the +UVB control, compared to the normal group (−UVB) without UV irradiation, the group treated with α-ionone exhibited a significant improvement on the thickness and depth of wrinkles, such as the deep wrinkles almost disappearing, and the like, compared to the +UVB control, even though the two groups were irradiated with the same UV intensity (see FIG. 5A). As a result of quantifying the degree of formation of wrinkles in the replica by using a computer image analyzer, the IO group exhibited significant decreases of 60%, 49%, 39%, and 68% in total wrinkle area, maximum wrinkle depth, mean depth, and mean length, respectively, compared to the +UVB control, and such efficacy of α-ionone on improving wrinkles was similar to a wrinkle improving effect observed with vitamin C (see FIG. 5B). The values shown in FIG. 5B denote mean±SEM of five mice, and a letter above each bar indicates a significant difference by one-way ANOVA followed by a Duncan's multiple range test ($p<0.05$). Thus, from the results, it can be confirmed that α-ionone intake has a significantly inhibitory effect on the formation of wrinkles by UV irradiation.

4) Changes in Skin Thicknesses of UV-Irradiated Hairless Mice

As photoaging proceeds by ultraviolet rays or the like, the formation of the stratum corneum increases to protect the skin dermis layer, resulting in the thickening of the skin, and the thickening of the skin epidermis layer due to UV irradiation means great damage to the skin due to the photoaging (Gail J., Molecular mechanism of skin ageing, Mech Ageing Dev 123: 801-810, 2002).

On the last day of the experimental rearing, the thickness of the dorsal skin was measured using a digital micro caliper. As a result, it was confirmed that the +UVB control exhibited a significant increase in skin thickness compared to the normal group (−UVB) without UV irradiation, and the group treated with α-ionone exhibited a significant decrease of 19% in skin thickness compared to the +UVB control (see FIG. 6A). The values shown in FIG. 6A denote mean±SEM of five mice, and a letter above each bar indicates a significant difference by one-way ANOVA followed by a Duncan's multiple range test ($p<0.05$).

Figure 6B:
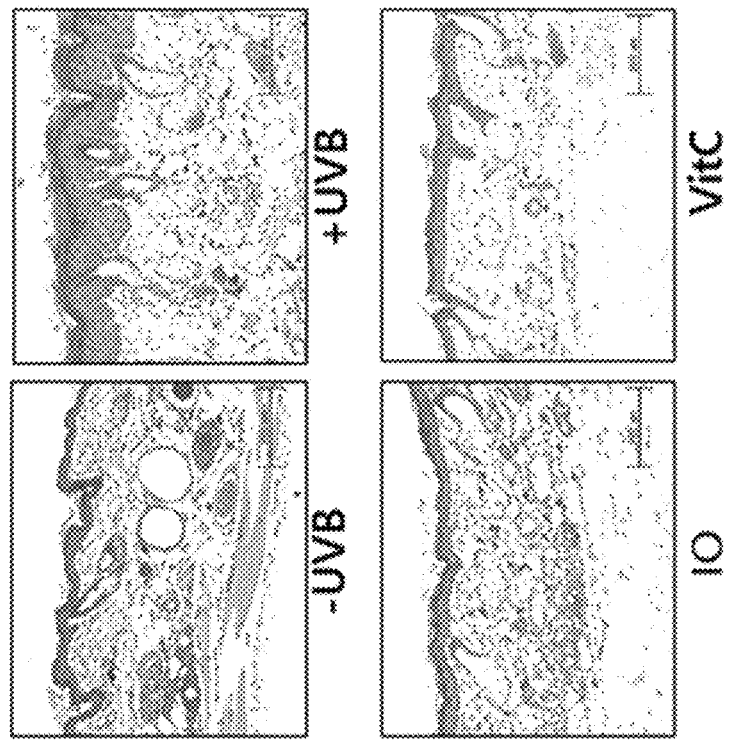
FIG. 6B illustrates images showing skin epidermis layers of the mice fed the experimental diets having the compositions shown in Table 1.
Figure 6A:
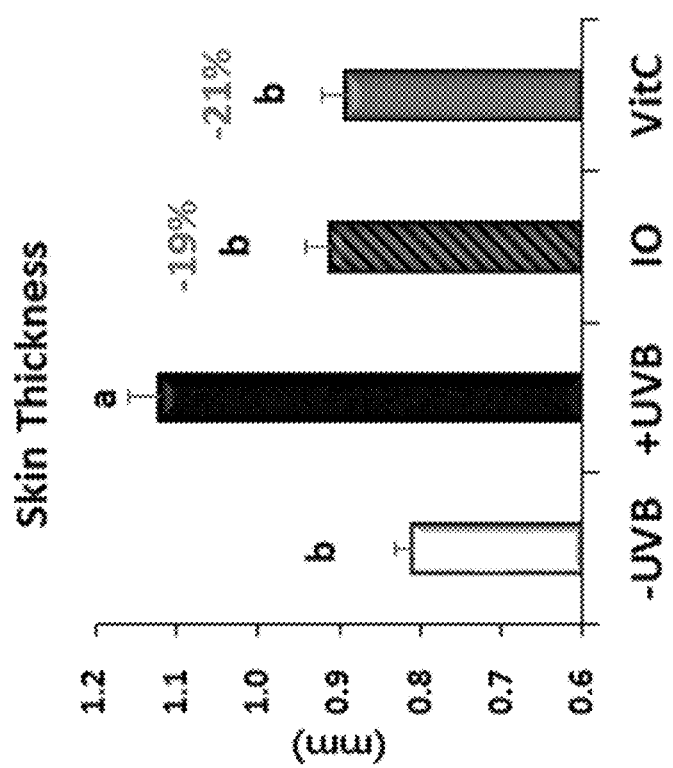
FIG. 6A is a graph showing measurement results of skin thicknesses of the mice fed the experimental diets having the compositions shown in Table 1.

Even in observation results of the thickness of the skin epidermis layer of each hairless mouse through H&E staining, the thickening of the skin epidermis layer was observed in the +UVB control compared to the normal group (−UVB) without UV irradiation, while the IO group exhibited a significant decrease in the thickness of the thickened epidermis layer due to UV irradiation (see FIG. 6B).

5) Quantitative and Morphological Changes of Collagen Fibers in Dermis Layers of UV-Irradiated Hairless Mice In the case of skin having undergone photoaging by UV irradiation, the collagen fiber network of the epidermis-dermis binding site is damaged, and therefore the amount and shape of the collagen fiber are used as a skin photoaging index (Varani et al. "Inhibition of type I procollagen synthesis by damaged collagen in photoaged skin and by collagenase-degraded collagen in vitro." The American journal of pathology 158: 931-942, 2001). The skin tissues of the hairless mice irradiated with ultraviolet rays were subjected to Masson's trichrome staining and a degree to which collagen fibers were stained was observed. As a result, collagen fibers strongly stained with aniline blue were observed in the dermis layer below the epidermis of the −UVB group, while collagen fibers of the +UVB group irradiated with UVB for 10 weeks were weakly stained with aniline blue. In the case of mice treated with α-ionone for 10 weeks while irradiated with UVB, collagen fibers of the dermis layer were relatively more compact and regularly arranged and a greater degree of staining by aniline blue was shown, which is similar to that of the normal group (−UVB), compared to the control irradiated with ultraviolet rays alone (see FIG. 7).

6) Changes in Gene Expression of Skin Tissues of UV-Irradiated Hairless Mice

Collagen types 1 and 3 are proteins that constitute matrix components of the dermis layer, and, in particular, collagen type 1 is present in the largest amount among the extracellular proteins existing in the skin connective tissue. Meanwhile, MMPs, which catalyze collagen decomposition, exist in 23 types in mammals. Among these, MMP types 1, 3 and 9 are known to increase by ultraviolet rays, and these three types of MMPs are enzymes that decompose collagen types 1 and 3. MMP-1 is known to cleave the middle of collagen fibers, while MMP-3 and MMP-9 are known to cleave the cleaved collagen fibers (Quan T. et al., Elevated matrix metalloproteinases and collagen fragmentation in photodamaged human skin: impact of altered extracellular matrix microenvironment on dermal fibroblast function. J Investigative Dermatology, 133: 1362, 2013; Kondo S. The roles of cytokines in photoaging. J Dermatological Science 23: S30-S36, 2000).

Changes in gene expression of the skin tissues were evaluated by RT-PCR analysis. As a result, the +UVB control exhibited a significant decrease in the expression of collagen types 1α1, α2, an 3α1 of the skin tissue and a significant increase in the expression of MMP-1a, MMP-1b, MMP-3 and MMP-9 genes, compared to the normal group (−UVB) without UV irradiation. Meanwhile, the group treated with α-ionone exhibited a significant increase in the expression of collagen types 1α1, α2, an 3α1 and a significant decrease in the expression of MMP-1a, MMP-1b, MMP-3 and MMP-9 genes, compared to the +UVB control (see FIG. 8). Thus, it is determined that α-ionone increases collagen protein synthesis in the skin tissue and inhibits decomposition of collagen fibers, thereby inhibiting the formation of wrinkles by UV irradiation.

The above-described results demonstrate that α-ionone has an effect of preventing or alleviating the formation of skin wrinkles due to ultraviolet rays, and thus may be usefully used as a material of functional cosmetics, health functional foods, pharmaceuticals, or quasi-drugs in the future.

Example 3

Sensory Test for Skin Wrinkle Improvement, Skin Irritation, and Skin Exfoliation 3-1. Preparation of α-Ionone-Containing Nutrition Cream (Experimental Example 1) and α-Ionone-Free Nutrition Cream (Comparative Example 1)

TABLE 3

| No. | Component | Experimental Example 1 (wt %) | Comparative Example 1 (wt %) |
|---|---|---|---|
| 1 | Cetearyl alcohol | 1.5 | 1.5 |
| 2 | Glyceryl stearate | 1 | 1 |
| 3 | Polysorbate 60 | 1.2 | 1.2 |
| 4 | Sorbitan sesquioleate | 0.3 | 0.3 |
| 5 | Cetyl octanoate | 6 | 6 |
| 6 | Squalane | 8 | 8 |
| 7 | Apricot Kernel oil | 4 | 4 |
| 8 | Dimethicone | 1 | 1 |
| 9 | Butylene glycol | 5 | 5 |
| 10 | Glycerin | 4 | 4 |
| 11 | Magnesium aluminum silicate | 0.2 | 0.2 |
| 12 | Xanthan gum | 0.05 | 0.05 |
| 13 | Antiseptic | Trace | Trace |
| 14 | Purified water | remainder | remainder |
| 15 | α-ionone | 1 | — |

Of the components identified by the respective component numbers in Table 3, components 1 to 8 were first melted by heating at a temperature of 70° C., and then emulsified in a solution prepared by dissolving and dispersing components 9 to 13 in component 14 and heating the resulting solution to 70° C. Subsequently, the emulsion was cooled down to a temperature of 56° C., and then component 15 dissolved in an aliquot of component 9 was added thereto, and the resulting solution was stirred and cooled at room temperature, thereby completing the preparation of an α-ionone-containing nutrition cream.

As Comparative Example 1, an α-ionone-free nutrition cream was prepared in the same manner using the same components as in Experimental Example 1, except that component 15, α-ionone, was not used.

3-2. Sensory Test for Wrinkle Improving Effect and Skin Irritation

To evaluate an effect of the cosmetic composition according to the present disclosure on improving skin wrinkles and skin irritation thereof, a sensory test was conducted using the nutrition creams prepared according to Experimental Example 1 and Comparative Example 1 of Table 3.

In particular, to measure skin wrinkle improving effects when each of the nutrition creams of Experimental Example 1 and Comparative Example 1 shown in Table 3 was applied on the skin, 20 females between the ages of 20 and 50 continuously used the nutrition cream of Experimental Example 1 of Table 3 (experimental group) on the left side of the face and the nutrition cream of Comparative Example 1 of Table 3 (control) on the right side of the face once a day for 12 weeks.

In the sensory test, in terms of the item for skin wrinkle improving effects, a wrinkle improving effect of the nutrition cream of Experimental Example 1 was evaluated relative to that of the nutrition cream of Comparative Example 1, and, for skin irritation evaluation, phenomena such as itching, burning, erythema, and the like of the skin were evaluated. The evaluation was performed according to a 5-point scoring method: excellent (5 points), very good (4 points), good (3 points), poor (2 points), and very poor (1 point), and the results thereof are shown in Table 4 below. In Table 4, a higher score in skin irritation indicates less skin irritation.

TABLE 4

| | Skin irritation | | Wrinkle improvement | |
|---|---|---|---|---|
| No. | Experimental Example 1 | Comparative Example 1 | Experimental Example 1 | Comparative Example 1 |
| 1 | 4 | 4 | 5 | 4 |
| 2 | 5 | 5 | 5 | 5 |
| 3 | 4 | 5 | 4 | 4 |
| 4 | 3 | 3 | 5 | 3 |
| 5 | 4 | 4 | 4 | 4 |
| 6 | 5 | 4 | 4 | 4 |
| 7 | 5 | 5 | 5 | 4 |
| 8 | 4 | 4 | 4 | 3 |
| 9 | 4 | 4 | 4 | 3 |
| 10 | 4 | 5 | 5 | 5 |
| 11 | 5 | 5 | 4 | 4 |
| 12 | 4 | 4 | 4 | 3 |
| 13 | 5 | 4 | 4 | 4 |
| 14 | 3 | 4 | 5 | 4 |
| 15 | 5 | 5 | 4 | 4 |
| 16 | 5 | 5 | 5 | 4 |
| 17 | 3 | 4 | 5 | 5 |
| 18 | 5 | 4 | 5 | 4 |
| 19 | 5 | 5 | 5 | 5 |
| 20 | 5 | 5 | 4 | 4 |
| Mean | 4.35 | 4.4 | 4.5 | 4.0 |

As shown in Table 4 above, it was confirmed that the score of skin irritation evaluation for the α-ionone-containing nutrition cream of Experimental Example 1 was 4.35, which was evaluated as excellent, and thus the nutrition cream of Experimental Example 1 exhibited a low degree of skin irritation similar to that of the nutrition cream of Comparative Example 1 evaluated as 4.4 points and, accordingly, had excellent skin safety.

In addition, it was confirmed that the skin wrinkle improving effect of the α-ionone-containing nutrition cream of Experimental Example 1 relative to that of the nutrition cream of Comparative Example 1 was evaluated as 4.5 points and thus had an excellent degree of wrinkle improvement.

Accordingly, the cosmetic composition of the present disclosure, including ionone or a cosmetically acceptable salt thereof as an active ingredient, has no side effects on the skin, and has an excellent effect of improving skin wrinkles, increasing collagen protein synthesis, and inhibiting collagen fiber decomposition and thus is highly effective in skin wrinkle improvement.

3-3. Test for Measuring Increase in Skin Moisturizing Ability

To measure a moisture retaining ability of the skin when each of the nutrition creams of Experimental Example 1 and Comparative Example 1 shown in Table 3 below was applied on the skin, 20 females between the ages of 20 and 50 applied the nutrition cream of Experimental Example 1 of Table 3 (experimental group) on the left side of the face and the nutrition cream of Comparative Example 1 of Table 3 (control) on the right side of the face, in sufficient amounts while softly massaging the skin. The massage was uniformly performed on the skin for about 1 minute.

A skin moisture content was measured using a Corneometer in a constant temperature-constant humidity chamber at a room temperature of 25° C. and a relative humidity of 45% before application, and the nutrition creams of Experimental Example 1 and Comparative Example 1 of Table 3 were applied on the left and right sides, respectively, of the face, followed by a rest period of 10 minutes, and skin moisture contents 12 hours and 24 hours after application were measured. A measuring device used was a moisture content measurer (Corneometer® CM 820, Courage+Khazaka electronic GmbH, Germany), which measures a moisturizing ability by measuring the capacitance of the skin according to moisture content of the skin. The Corneometer measures the moisturizing ability by measuring the amount of ions of moisture present in the epidermis of the skin and quantifying the amount to calculate the amount of the moisture, and the measurement method is as follows.

1) A Corneometer probe was placed on a skin part to be measured.

2) When the skin was pressed by the probe, the capacitance of the skin was quantified through a sensor and displayed on the screen.

3) The measurement processes were repeated by varying sites to be measured.

4) After one measurement, the sensor was wiped with a disposable wipe such as Kimwipes, and then measurement was performed again.

The values measured are mean values and shown in Table 5 below.

TABLE 5

| | Skin moisture content (%) | | |
|---|---|---|---|
| Experimental material | Before application | 12 hours thereafter | 24 hours thereafter |
| Experimental Example 1 | 30.0 | 44.1 | 38.5 |
| Comparative Example 1 | 30.2 | 37.6 | 30.5 |

As shown in the above-described results, it can be confirmed that, when the nutrition cream of Comparative Example 1 was applied, the skin moisture content was increased to some extent 12 hours after application, while returning to a level similar to the state before application, 24 hours after application. In contrast, it was confirmed that, when the α-ionone-containing nutrition cream of Experimental Example 1 was applied on the skin, the moisturizing ability thereof lasted for over 24 hours and an effect thereof on increasing skin moisture content was also greater than that of the nutrition cream of Comparative Example 1.

3-4. Skin Exfoliation Effect Test

To measure skin exfoliation effects when each of the nutrition creams of Experimental Example 1 and Comparative Example 1 shown in Table 3 above was applied on the skin, 20 females between the ages of 20 and 50 applied the nutrition cream of Experimental Example 1 of Table 3 (experimental group) on the left side of the face and the nutrition cream of Comparative Example 1 of Table 3 (control) on the right side of the face, in sufficient amounts while softly massaging the skin. The massage was uniformly performed on the skin for about 1 minute.

To measure the amount of dead skin cells, an initial amount of dead skin cells was measured using Charm view (Moritex, Japan) in a constant temperature-constant humidity chamber at a room temperature of 25° C. and a relative humidity of 45% before application. The formulations of Experimental Example 1 and Comparative Example 1 of Table 3 were applied on the left and right sides, respectively, of the face, and then the amount of dead skin cells at 24 hours after application was measured and a decreased amount of the dead skin cells was calculated. The values calculated are mean values and shown in Table 6 below.

TABLE 6

| | Amount of dead skin cells (%) | | |
|---|---|---|---|
| Experimental material | Before application | 24 hours after application | Decreased amount of dead skin cells |
| Experimental Example 1 | 20.3 | 10.3 | 10.0 |
| Comparative Example 1 | 20.3 | 16.1 | 4.2 |

As shown in the above-described results, it was confirmed that the α-ionone-containing nutrition cream of Experimental Example 1 exhibited a greater effect of decreasing dead skin cells than that of the α-ionone-free nutrition cream of Comparative Example 1. As the moisturizing effect is imparted into the skin, the amount of dead skin cells is decreased, and it is determined that, as verified in Example 3-3 above, the nutrition cream of Experimental Example 1 exhibited a greater effect of decreasing dead skin cells than that of the nutrition cream of Comparative Example 1 due to an excellent moisture retaining ability thereof.

[Preparation Example 1] Preparation of Cosmetics 1-1. Preparation of Skin Softener A skin softener including α-ionone was prepared with the composition shown in Table 7 below.

TABLE 7

| Composition | Preparation Example 1-1 (wt %) |
|---|---|
| α-ionone | 0.1 |
| ethanol | 10.0 |
| Polylauric acid Polyoxyethylene sorbitan | 1.0 |
| Paraoxybenzoic acid methyl | 0.2 |
| Glycerin | 5.0 |
| 1,3-butylene glycol | 6.0 |
| Fragrance | Appropriate amount |
| Pigment | Appropriate amount |

1-2. Preparation of Nutrition Lotion

A nutrition lotion including α-ionone was prepared with the composition shown in Table 8 below.

TABLE 8

| Composition | Preparation Example 1-2 (wt %) |
|---|---|
| α-ionone | 0.05 |
| Vaseline | 2.0 |
| Sesquioleic acid sorbitan | 0.8 |
| Polyoxyethylene oleylethyl | 1.2 |
| Paraoxybenzoic acid methyl | Appropriate amount |
| Propylene glycol | 5.0 |
| Ethanol | 3.2 |
| Carboxyvinyl polymer | 18.0 |
| Potassium hydroxide | 0.1 |
| Pigment | Appropriate amount |
| Fragrance | Appropriate amount |

1-3. Preparation of Nutrition Cream

A nutrition cream including α-ionone was prepared with the composition shown in Table 9 below.

TABLE 9

| Composition | Preparation Example 1-3 (wt %) |
| --- | --- |
| α-ionone | 0.2 |
| Stearic acid | 15.0 |
| Cetanol | 1.0 |
| Potassium hydroxide | 0.7 |
| Glycerin | 5.0 |
| Propylene glycol | 3.0 |
| Preservative | Appropriate amount |
| Fragrance | Appropriate amount |
| Purified water | To 100 |

1-4. Preparation of Pack

A pack including α-ionone was prepared with the composition shown in Table 10 below.

TABLE 10

| Composition | Preparation Example 1-4 (wt %) |
| --- | --- |
| α-ionone | 0.05 |
| Glycerin | 5.0 |
| Propylene glycol | 4.0 |
| Polyvinyl alcohol | 15.0 |
| Ethanol | 8.0 |
| Polyoxyethylene oleyl ethyl | 1.0 |
| Paraoxybenzoic acid methyl | 0.2 |
| Pigment | Appropriate amount |
| Fragrance | Appropriate amount |

1-5. Preparation of Essence

An essence including α-ionone was prepared with the composition shown in Table 11 below.

TABLE 11

| Composition | Preparation Example 1-5 (wt %) |
| --- | --- |
| α-ionone | 0.2 |
| Propylene glycol | 10.0 |
| Glycerin | 10.0 |
| Aqueous sodium hyaluronate solution (1%) | 5.0 |
| Ethanol | 5.0 |
| Polyoxyethylene hardened castor oil | 1.0 |
| Paraoxybenzoic acid methyl | 0.1 |
| Fragrance | Appropriate amount |
| Purified water | To 100 |

[Preparation Example 2] Preparation of Health Functional Food 2-1. Preparation of Health Functional Food A health functional food including α-ionone was prepared with the composition shown in Table 12 below.

TABLE 12

| Composition | Preparation Example 2-1 |
| --- | --- |
| α-ionone | 1000 mg |
| Vitamin mixture | Appropriate amount |
| Vitamin A acetate | 1.0 mg |
| Vitamin E | 0.13 mg |
| Vitamin B1 | 0.15 mg |
| Vitamin B2 | 0.5 mg |
| Vitamin B6 | 0.2 μg |
| Vitamin B12 | 10 mg |
| Vitamin C | 10 μg |
| Biotin | 1.7 mg |
| Nicotinic acid amide | 50 μg |
| Folic acid | 0.5 mg |
| Calcium pantothenate | Appropriate amount |
| Mineral mixture | Appropriate amount |
| Ferrous sulfate | 1.75 mg |
| Zinc oxide | 0.82 mg |
| Magnesium carbonate | 25.3 mg |
| Monobasic potassium phosphate | 15 mg |
| Dibasic potassium phosphate | 55 mg |
| Potassium citrate | 90 mg |
| Calcium carbonate | 100 mg |
| Magnesium chloride | 24.8 mg |

Although ingredients relatively suitable for use in health functional foods are mixed in a composition ratio of the vitamin and mineral mixture as an exemplary embodiment, the mixing ratio may be arbitrarily varied. In addition, the above-listed ingredients may be mixed according to a general method of preparing a health functional food, and then prepared into granules, which may then be used for the preparation of a health functional food composition according to a general method.

2-2. Preparation of Health Drink

A health drink including α-ionone was prepared with the composition shown in Table 13 below.

TABLE 13

| Composition | Preparation Example 2-2 (mg) |
| --- | --- |
| α-ionone | 1000 mg |
| Citric acid | 1000 mg |
| Oligosaccharide | 100 g |
| Green plum concentrate | 2 g |
| Taurine | 1 g |
| Purified water | Appropriate amount |

The above-listed ingredients are mixed according to a general method of preparing a health drink, the mixture is heated and stirred at 85° C. for about 1 hour to prepare a solution, the solution is filtered, the filtrate is collected in 2l sterilized containers and then sealed and sterilized, followed by refrigerated storage, which is then used for the preparation of a heath drink composition according to the present disclosure. Although ingredients relatively suitable for use in favorite beverages are mixed in the above-described composition ratio as an exemplary example, the mixing ratio may be arbitrarily varied depending on local and national preferences such as demand classes, demand countries, purposes of use, and the like.

2-3. Preparation of Tablets

Tablets including α-ionone were prepared with the composition shown in Table 14 below according to a general method of preparing tablets.

TABLE 14

| Composition | Preparation Example 2-3 (mg) |
| --- | --- |
| α-ionone | 100 mg |
| Corn starch | 100 mg |
| Lactose | 100 mg |
| Magnesium stearate | 2 mg |

2-4. Preparation of Capsules

Capsules including α-ionone were prepared with the composition shown in Table 15 below such that a gelatin capsule was filled with the above ingredients according to a general method of preparing capsules.

TABLE 15

| Composition | Preparation Example 2-4 (mg) |
| --- | --- |
| α-ionone | 100 mg |
| Corn starch | 100 mg |
| Lactose | 100 mg |
| Magnesium stearate | 2 mg |

2-5. Preparation of Pills

Pills were prepared with the composition shown in Table 16 below according to a general method of preparing pills to a weight of 4 g per pill.

TABLE 16

| Composition | Preparation Example 2-5 (mg) |
| --- | --- |
| α-ionone | 1 g |
| Lactose | 1.5 g |
| Glycerin | 1 g |
| Xylitol | 0.5 g |

2-6. Preparation of Granules

Granules were prepared with the composition shown in Table 17 below such that 100 mg of 30% ethanol was added to the above ingredients and the resulting solution was dried at 60° C. to form granules, and then a container was filled therewith.

TABLE 17

| Composition | Preparation Example 2-6 (mg) |
| --- | --- |
| α-ionone | 150 mg |
| Soybean extract | 50 mg |
| Glucose | 200 mg |
| Starch | 600 mg |

Preparation Example 3

Preparation of Ointment for External Application to Skin

An ointment for external application to the skin, including α-ionone, was prepared with the composition shown in Table 18 below.

TABLE 18

| Composition | Preparation Example 3 (wt %) |
| --- | --- |
| α-ionone | 0.5 |
| Diethyl sebacate | 8.0 |
| Hard lead | 5.0 |
| Polyoxyethylene oleyl ether phosphate | 6.0 |
| Sodium benzoate | Appropriate amount |

As is apparent from the foregoing description, a composition including ionone or a salt thereof as an active ingredient according to the present disclosure has a high activity of enhancing skin moisture content, reducing skin moisture evaporation, increasing procollagen secretion, promoting collagen biosynthesis, suppressing collagen fiber damage, suppressing collagen fiber decomposition, inhibiting erythema, and suppressing the thickening of a skin epidermis layer, and thus may be usefully used to enhance skin moisturizing, exfoliate skin, enhance skin elasticity, inhibit erythema, reduce skin wrinkles, and/or alleviate skin photoaging. In addition, the ionone of the present disclosure is a natural substance, and thus has no harm and few side effects with respect to the human body and, accordingly, may be widely used as a material for cosmetics, health functional foods, drugs or quasi-drugs, and the like.

It will be apparent to those skilled in the art that various modifications can be made to the above-described exemplary embodiments of the present disclosure without departing from the spirit or scope of the invention. Thus, it is intended that the present disclosure covers all such modifications provided they come within the scope of the appended claims and their equivalents.

What is claimed is:

1. A method of enhancing skin moisturizing, exfoliating skin, improving skin elasticity, inhibiting erythema, improving skin wrinkles, and/or alleviating skin photoaging, the method comprising administering or taking a composition comprising:
a skin active ingredient consisting of ionone or a pharmaceutically acceptable or consisting of ionone or a pharmaceutically acceptable salt thereof and vitamin C; and
a carrier,
wherein the composition i) increases the level of PIP (procollagen type I C-peptide), ii) increases the expression level of Collagen Type 1α1, 1α2, 3α1, or iii) decreases the expression level of MMP-1a, MMP-3, and MMP-9.

2. The method according to claim 1, wherein the composition is cosmetic composition, health functional food composition, pharmaceutical or quasi-drug composition.

3. The method according to claim 2, wherein the cosmetic composition is prepared in any one formulation selected from the group consisting of a skin lotion, a skin softener, a skin toner, an astringent, a lotion, a milk lotion, a moisturizing lotion, a nutrition lotion, a massage cream, a nutrition cream, a moisturizing cream, a hand cream, an essence, a pack, a mask pack, a mask sheet, an exfoliating agent, a soap, a shampoo, a cleansing foam, a cleansing lotion, a cleansing cream, a body lotion, a body cleanser, an emulsion, a press powder, a loose powder, and an eye shadow.

4. The method according to claim 2, wherein the health functional food composition is prepared in any one formulation selected from the group consisting of tablets, granules, powder, capsules, a liquid solution, and pills.

5. The method according to claim 1, wherein an amount of the ionone or the pharmaceutically acceptable salt thereof ranges from about 0.0001 wt % to about 20 wt % with respect to a total weight of the composition.

* * * * *

UNITED STATES PATENT AND TRADEMARK OFFICE
CERTIFICATE OF CORRECTION

PATENT NO. : 10,137,070 B2
APPLICATION NO. : 15/629517
DATED : November 27, 2018
INVENTOR(S) : Tae Sun Park Page 1 of 1

It is certified that error appears in the above-identified patent and that said Letters Patent is hereby corrected as shown below:

In the Claims

<u>Claim 1, Column 33, Line 18:</u>
Insert -- salt thereof -- before "or consisting of"

Signed and Sealed this
Twelfth Day of February, 2019

Andrei Iancu
*Director of the United States Patent and Trademark Office*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: Collagen type 1 alpha 1 forward primer

<400> SEQUENCE: 1
ggcaacagtc gcttcaccta                                          20

<210> SEQ ID NO 2
<211> LENGTH: 20
<212> TYPE: DNA
<213> ORGANISM: Artificial
<220> FEATURE:
<223> OTHER INFORMATION: Collagen type 1 alpha 1 reverse primer

<400> SEQUENCE: 2
agtccgaatt cctggtctgg                                          20

<210> SEQ ID NO 3
<211> LENGTH: 20
```

```
<212> TYPE: DNA
<213> ORGANISM: Artificial
<220> FEATURE:
<223> OTHER INFORMATION: Collagen type 1 alpha 2 forward primer

<400> SEQUENCE: 3
cggttctgtt ggtcctgttg                                              20

<210> SEQ ID NO 4
<211> LENGTH: 20
<212> TYPE: DNA
<213> ORGANISM: Artificial
<220> FEATURE:
<223> OTHER INFORMATION: Collagen type 1 alpha 2 reverse primer

<400> SEQUENCE: 4
acccctgtgc cctttatcac                                              20

<210> SEQ ID NO 5
<211> LENGTH: 20
<212> TYPE: DNA
<213> ORGANISM: Artificial
<220> FEATURE:
<223> OTHER INFORMATION: Collagen type 3 alpha 1 forward primer

<400> SEQUENCE: 5
taaccaaggc tgcaagatgg                                              20

<210> SEQ ID NO 6
<211> LENGTH: 20
<212> TYPE: DNA
<213> ORGANISM: Artificial
<220> FEATURE:
<223> OTHER INFORMATION: Collagen type 3 alpha 1 reverse primer

<400> SEQUENCE: 6
accagtgctt acgtgggaca                                              20

<210> SEQ ID NO 7
<211> LENGTH: 20
<212> TYPE: DNA
<213> ORGANISM: Artificial
<220> FEATURE:
<223> OTHER INFORMATION: MMP-1a forward primer

<400> SEQUENCE: 7
ccctgtgttt cacaacggag                                              20

<210> SEQ ID NO 8
<211> LENGTH: 20
<212> TYPE: DNA
<213> ORGANISM: Artificial
<220> FEATURE:
<223> OTHER INFORMATION: MMP-1a reverse primer

<400> SEQUENCE: 8
cctcagcttt tcagccatca                                              20

<210> SEQ ID NO 9
<211> LENGTH: 20
<212> TYPE: DNA
<213> ORGANISM: Artificial
<220> FEATURE:
<223> OTHER INFORMATION: MMP-1b forward primer

<400> SEQUENCE: 9
```
tttgctcatg cttttctgcc                                          20

<210> SEQ ID NO 10
<211> LENGTH: 20
<212> TYPE: DNA
<213> ORGANISM: Artificial
<220> FEATURE:
<223> OTHER INFORMATION: MMP-1b reverse primer

<400> SEQUENCE: 10
gaatgggaga gtccaaggga                                          20

<210> SEQ ID NO 11
<211> LENGTH: 20
<212> TYPE: DNA
<213> ORGANISM: Artificial
<220> FEATURE:
<223> OTHER INFORMATION: MMP-3 forward primer

<400> SEQUENCE: 11
tgctggtatg gagcttctgc                                          20

<210> SEQ ID NO 12
<211> LENGTH: 20
<212> TYPE: DNA
<213> ORGANISM: Artificial
<220> FEATURE:
<223> OTHER INFORMATION: MMP-3 reverse primer

<400> SEQUENCE: 12
catctccaac ccgaggaact                                          20

<210> SEQ ID NO 13
<211> LENGTH: 20
<212> TYPE: DNA
<213> ORGANISM: Artificial
<220> FEATURE:
<223> OTHER INFORMATION: MMP-9 forward primer

<400> SEQUENCE: 13
gtggaccatg aggtgaacca                                          20

<210> SEQ ID NO 14
<211> LENGTH: 20
<212> TYPE: DNA
<213> ORGANISM: Artificial
<220> FEATURE:
<223> OTHER INFORMATION: MMP-9 reverse primer

<400> SEQUENCE: 14
actgcacggt tgaagcaaag                                          20

<210> SEQ ID NO 15
<211> LENGTH: 20
<212> TYPE: DNA
<213> ORGANISM: Artificial
<220> FEATURE:
<223> OTHER INFORMATION: GAPDH forward primer

<400> SEQUENCE: 15
ggagattgtt gccatcaacg                                          20

<210> SEQ ID NO 16
<211> LENGTH: 20
<212> TYPE: DNA
<213> ORGANISM: Artificial

```
<220> FEATURE:
<223> OTHER INFORMATION: GAPDH reverse primer

<400> SEQUENCE: 16
tgacaagctt cccattctcg                                               20
```